United States Patent [19]

Sun et al.

[11] Patent Number: 6,149,774
[45] Date of Patent: Nov. 21, 2000

[54] AC WAVEFORMS BIASING FOR BEAD MANIPULATING CHUCKS

[75] Inventors: Hoi Cheong Steve Sun, Monmouth Junction; Eugene Samuel Poliniak, Willingboro; Dominic Stephen Rosati, Hamilton; Bawa Singh, Voorhees; Nitin Vithalbhai Desai, Princeton Junction, all of N.J.

[73] Assignee: Delsys Pharmaceutical Corporation

[21] Appl. No.: 09/095,425

[22] Filed: Jun. 10, 1998

[51] Int. Cl.⁷ ....................................................... B01J 19/08
[52] U.S. Cl. ................... 204/164; 422/186.04; 427/2.14; 118/624; 118/DIG. 2
[58] Field of Search ....................... 204/164; 422/186.04; 427/2.14; 118/DIG. 2, 624

[56] References Cited

U.S. PATENT DOCUMENTS

| Re. 30,401 | 9/1980 | White | 204/192 |
|---|---|---|---|
| 2,408,143 | 4/1946 | Huebner . | |
| 3,831,606 | 8/1974 | Damani | 128/266 |
| 3,971,377 | 7/1976 | Damani | 128/266 |
| 4,047,525 | 9/1977 | Kulessa et al. | 128/208 |
| 4,072,129 | 2/1978 | Bright et al. | 118/629 |

(List continued on next page.)

FOREIGN PATENT DOCUMENTS

| 57-196211 | 2/1982 | Japan . |
|---|---|---|
| 92/09505 | 5/1993 | WIPO . |
| 93/09751 | 4/1994 | WIPO . |
| 93/01053 | 6/1994 | WIPO . |
| 94/03569 | 10/1994 | WIPO . |
| 94/00633 | 1/1995 | WIPO . |

OTHER PUBLICATIONS

J. –F. Davier et al., *Electrostatic Clamping Applied to Semiconductor Plasma Processing*, I. Theoretical Modeling, J. Electrochem. Soc., vol. 140, No. 11, pp. 3245–3256 (Nov. 1993).

J. –F. Davier et. al., *Electrostatic Clamping Applied to Semiconductor Plasma Processing*, II. Experimental Results, J. Electrochem. Soc., vol. 140, No. 11, pp. 3256–3261 (Nov. 1993).

John Field, *Electrostatic Wafer Clamping For Next–Generation Manufacturing*, Solid State Technology, pp. 91–98 (Sep. 1994).

Larry D. Hartsough, *Electrostatic Wafer Holding*, Solid State Technology, pp. 87–90 (Jan. 1993).

Mamoru Nakasuji et al., *Low Voltage And High Speed Operating Electrostatic Wafer Chuck Using Sputtered Tantalum Oxide Membrane*, J. Vac. Sci. Technol, A, vol. 12, No. 5, pp. 2834–2839 (Sep./Oct. 1994).

Donald A. Seanor, *Triboelectrification Of Polymers in K.C. Frisch and A. Patsis*, Electrical Properties of Polymer (Technomic Publications, Westport, CT), pp. 37–58 (1989) no month available.

Peter Singer, *Electrostatic Chucks in Wafer Processing*, Semiconductor International, pp. 57–64 (Apr. 1995).

T. Watanabe et. al., *Electrostatic Charge Distribution In The Dielectric Layer Of Alumina Electrostatic Chuck*, Jouurnal of Materials Science, vol. 29, pp. 3510–3516 (1994) no month available.

Toshiya Watanabe et. al., *Electrostatic Force and Absorption Current of Alumina Electrostatic Chuck*, Jpn. J. Appl. Phys., vol. 31, pt. 1, No. 7, pp. 2145–2150 (Jul. 1992).

Primary Examiner—Kishor Mayekar
Attorney, Agent, or Firm—Dechert Price & Rhoads

[57] ABSTRACT

AC waveforms biasing of bead transporter chucks and their accumulated charge sensing circuits tailored for low resistivity substrates and beads where if traditional DC quasi-static biasing potentials were used, the bead attraction potentials of the chuck would undergo rapid RC decay and cause the bead transporter chuck to stop working. Methods for selecting AC waveforms are given, including those that maximize the time average of the bead attraction potential at the bead collection zone of the bead contact surface.

22 Claims, 5 Drawing Sheets

U.S. PATENT DOCUMENTS

| | | | |
|---|---|---|---|
| 4,160,257 | 7/1979 | Carrish | 346/159 |
| 4,197,289 | 4/1980 | Sturzenegger et al. | 424/21 |
| 4,332,789 | 6/1982 | Mlodozeniec | 424/27 |
| 4,349,531 | 9/1982 | Mlodozeniec et al. | 424/27 |
| 4,502,094 | 2/1985 | Lewin et al. | 361/234 |
| 4,538,163 | 8/1985 | Sheridon | 346/155 |
| 4,554,611 | 11/1985 | Lewin | 361/234 |
| 4,570,630 | 2/1986 | Elliott et al. | 128/203.15 |
| 4,627,432 | 12/1986 | Newell et al. | 128/203.15 |
| 4,628,227 | 12/1986 | Briere | 315/111.81 |
| 4,652,318 | 3/1987 | Masuda et al. | 156/89 |
| 4,664,107 | 5/1987 | Wass | 128/200.23 |
| 4,685,620 | 8/1987 | Law et al. | 239/3 |
| 4,795,644 | 1/1989 | Zentner | 424/468 |
| 4,811,731 | 3/1989 | Newell et al. | 128/203.15 |
| 4,860,417 | 8/1989 | Tajima et al. | 29/130 |
| 4,889,114 | 12/1989 | Kladders | 128/203.15 |
| 4,917,978 | 4/1990 | Ritt et al. | 430/23 |
| 4,918,468 | 4/1990 | Miekka et al. | 346/159 |
| 4,921,727 | 5/1990 | Datta et al. | 427/57 |
| 4,921,767 | 5/1990 | Datta et al. | 430/23 |
| 4,925,701 | 5/1990 | Jansen et al. | 427/38 |
| 4,971,257 | 11/1990 | Birge | 239/708 |
| 4,992,807 | 2/1991 | Thomson | 346/155 |
| 5,014,076 | 5/1991 | Caley, Jr. et al. | 346/159 |
| 5,027,136 | 6/1991 | Fotland et al. | 346/159 |
| 5,028,501 | 7/1991 | Ritt et al. | 430/23 |
| 5,031,610 | 7/1991 | Armstrong et al. | 128/200.23 |
| 5,080,380 | 1/1992 | Nakagawa et al. | 279/1 M |
| 5,115,803 | 5/1992 | Sioutas | 128/200.23 |
| 5,161,524 | 11/1992 | Evans | 128/203.15 |
| 5,176,132 | 1/1993 | Drought et al. | 128/203.15 |
| 5,186,164 | 2/1993 | Raghuprasad | 128/200.14 |
| 5,239,993 | 8/1993 | Evans | 128/203.15 |
| 5,243,970 | 9/1993 | Ambrosio et al. | 128/203.15 |
| 5,263,475 | 11/1993 | Altermatt et al. | 128/203.15 |
| 5,278,588 | 1/1994 | Kubelik | 346/159 |
| 5,301,666 | 4/1994 | Lerk et al. | 128/203.15 |
| 5,327,883 | 7/1994 | Williams et al. | 128/203.15 |
| 5,328,539 | 7/1994 | Sato | 156/275.5 |
| 5,377,071 | 12/1994 | Moslehi | 361/234 |
| 5,463,525 | 10/1995 | Barnes et al. | 361/234 |
| 5,499,487 | 3/1996 | McGill | 53/473 |
| 5,522,131 | 6/1996 | Steger | 29/829 |
| 5,534,309 | 7/1996 | Liu | 427/458 |
| 5,619,984 | 4/1997 | Hodson et al. | 128/203.15 |
| 5,642,727 | 7/1997 | Datta | 128/203.15 |
| 5,647,347 | 7/1997 | Van Oort | 128/203.15 |
| 5,669,973 | 9/1997 | Pletchs | 118/624 |
| 5,714,007 | 2/1998 | Pletcher et al. | 118/629 |
| 5,788,814 | 8/1998 | Sun et al. | 204/297 R |

AC WAVEFORMS BIASING FOR BEAD MANIPULATING CHUCKS

The present invention is directed to devices for electrically picking up and dispensing grains in a spatially resolved manner. Specifically, this disclosure describes novel operation techniques and bead attraction electrode biasing for bead transporter chucks. The invention provides for the application of dynamic electric fields, such as those obtained using periodic pulses or other AC waveform components, to bead attraction electrodes in lieu of quasi-static electric fields that were used previously to attract grains in bead manipulating chucks. These dynamic potentials can be used not only for attracting and retaining grains, but in grain deposition sensing by measuring accumulated charge.

Electrostatic bead transporter chucks may be used to pick up, manipulate, transport, and then discharge or place grains or objects for use in creating pharmaceutical, diagnostic or chemical compositions, or in performing assays or chemical analysis.

Bead transporter chucks act as clamps to hold or retain an object or objects. Bead transporter chucks provide superior performance for manipulating grains, such as beads with diameters of 100–300 microns in chemical synthesis, such as combinatorial chemistry for solid phase synthesis, or in an assay using PCR (polymerase chain reaction) or other materials such as powders, such as can be used to deposit pharmaceuticals on a substrate.

For example, bead transporter chucks allow deposition of grains on an array in a manner that is faster and more reliable than by the use of micropipettes, which can be inefficient, tedious, and time consuming. Another application for bead transporter chucks is synthesis of pharmaceutical compositions, especially when used to combine compounds to form compositions to be packaged into administration forms for humans or animals.

Grains containing one or more active ingredients may be deposited onto well known carriers or substrates to make pharmaceutical dosage forms. Such grains may take the form, for example, of [1] a powder, such as dry micronized forms made by air jet milling processes; [2] microspheres; [3] extremely small structures, including fullerenes, chelates, or nanotubes; or [4] liposomes and fatty droplets formed from lipids or cell membranes.

The use of bead transporter chucks provides a customized and precise method for formulating drug compositions. The transporter can be used when merging adjacent substrates carrying active ingredient to form multidosage packs, in which dosage may decrease or increase from one individual unit to the next, as in hormone-based (e.g., birth control) drugs or antibiotic remedies. Using an electrostatic bead transporter chuck, dosages may be easily established or determined by the number and/or type of grains dispensed onto each pharmaceutical carrier, or by using electrical, optical, or mechanical dosage sensing. Using bead transporter chucks to place active ingredients into pharmaceutical compositions can give high repeatability and is also advantageous when the active ingredients are not compatible, such as when the active ingredient is poorly soluble with carriers, or where a formulation or carrier negatively affects the bioavailability or stability of the active ingredient.

Although emphasis is placed in this disclosure on use of electrostatic bead transporter chucks that apply electric fields for grain retention and/or release, the teachings given here can be applied to chucks that also use other phenomena, such as the use of compressed gas or vacuum, or electrically/chemically switchable adhesives, in controlling grains and/or substrates. Electrostatic or quasi-electrostatic holding mechanisms, however, are far more benign to delicate grain structures than traditional mechanical techniques, particularly when manipulating biologically active compounds where crushing, contamination, or oxidative damage must be minimized or eliminated.

The present invention can involve use of acoustic stimulation or acoustic dispensers, where acoustic energy, provided by a speaker or piezoelectric device, is used to great advantage in grain control, that is, propelling and/or tribocharging grains prior to, and especially during, electrostatic manipulation. Tribocharging grains, as known in the art, and described below, is more efficient and less damaging to the grains than corona or plasma charging, which typically requires high applied voltages of around 5 kV. Often, the sonically vibrating membrane or mesh used in such an acoustic grain dispenser can itself be used to tribocharge the particles, eliminating the need to charge the grains prior to their entry into the acoustic dispenser. The use of acoustic dispensers allows polarity discrimination of grains, where wrongly charged grains are discouraged from being retained by the bead transporter chuck. Other forms of charging and dispensing the grains can be used, such as those described in U.S. application Ser. No. 09/095,246, filed Jun. 10, 1998, pending. This concurrently filed application describes grain feed systems that use augers, jet mills or fluidized beds, gas-driven Venturi, and induction charging in grain feed tubing.

Many bead transporter chucks offer precision in being able to have one, and only one grain attracted, transported, and discharged for each bead transporter chuck, or for each well, pixel, or individual spatial element of the bead transporter chuck. In many cases, each pixel can be considered a tiny bead transporter chuck that is selectively and independently controlled, such as planar chucks having individually addressable x and y coordinates. This includes individually addressable pixels for different (multiple) grain types.

Grains manipulated by these bead transporter chucks (or bead manipulating chucks) can be easily and controllably releasable, with wrongly charged grains (objects or grains having a charge of the opposite polarity desired) not occupying bead retaining or collection zones on the bead transporter chuck. They function well for a wide range of grain diameters, including grains with general dimensions of 100 microns and up, grains of much smaller dimensions, and also including porous or hollow grains that have high charge/mass ratios. They also offer durability and re-usability, and good ease-of-use, including having selectively or wholly transparent elements for easy movement and alignment of the chuck with intended targets or carriers.

Often, instead of depositing grains singly, bead transporter chucks are used to attract and place powder, such as powder containing active ingredient, on a substrate, such an edible substrate used for pharmaceutical dosage forms.

Electrodes used for attracting grains can be directly exposed, or covered by a dielectric, to prevent ionic breakdown (sparking) in air and to make use of the properties of dielectric to enhance grain holding capacity. To control the amount of charged grains that may be attracted, an indirect method can be used where an attraction electrode is not used directly to attract grains—but rather is used to capacitively couple, as discussed below, to a pad or floating electrode. This floating electrode then develops image charges partly in response to the field generated by the bead electrode, and its operation is self limiting in that it can only serve to attract a finite amount of charge before the potential it generates is cancelled. This indirect charging method can be more gentle, more precise, and less expensive to implement than charging by corona discharge, particularly for high resolution applications. The instant invention can be applied to any number of bead transporter chuck designs, but for illustration purposes, the chuck shown here attracts grains indirectly by way of one or more floating electrodes. Other useful electrode designs are illustrated in U.S. application Ser. No. 09/095,246, filed Jun. 10, 1998. Further techniques employed for precise dosage control include the use of sensing electrodes used for grain deposition sensing. Sensing electrodes can be thought of as equivalent to bead transporter chucks dedicated to, and specially monitored for accumulated grain charge.

However, bead transporter chuck designs and operation techniques that use simple static or quasi-static direct current (DC) potentials applied to attraction electrodes to pick up and discharge grains can, under certain conditions, encounter serious problems with grain attraction and charge control.

One problem encountered is the conductivity of resistive substrates does not allow for charge retention needed for attracting grains or powder to the substrates. Previous chucks were designed initially for use with quasi-static DC bias conditions, with selective application of DC potentials to bead attraction electrodes for grain pickup. Generally, polarities were reversed to aid in grain discharge only. These chucks using quasi-static grain attraction voltages were well suited for grains (e.g., powders) and substrates possessing high resistivity, such as insulators or polymeric films having a bulk resistivity $\rho$ on the order of about $10^{15}$ $\Omega$-cm.

Unfortunately, many bead transporter chucks using quasi-static DC potentials applied to grain attracting electrodes are simply not responsive or effective for lower resistivity grains or substrates. Because of the higher conductivity of low resistivity grains or substrates, DC or quasi-staticly generated charges within the grain or substrate decay rapidly using higher conductivity substrates or grain compositions. This rapid decay or leakage of charge comes about through internal movement of charges within the grain or substrate and by stray leakage, often aided by ambient humidity. This makes the bead transporter chuck useless in attracting and retaining higher conductivity grains or powders. In using, for example, a bead transporter chuck employing capacitive coupling to a floating electrode, there is only a finite amount of charge-inducing and attraction capacity available. With lower resistivity beads or substrates, the induced-charge gathering potential on areas adjacent to the floating pad, such as on a substrate, can decay to zero in a matter of a few milliseconds—and this is usually not enough time to accelerate, transport, and retain grains in intended bead collection zones.

Specifically, this invention addresses problems encountered with substrates having insufficient resistivity p, such as substrates having bulk resistivities $\rho$ of $10^{10}$ or $10^{11}$ $\Omega$-cm. As discussed below, the circuit elements in many bead transporter chucks have electrical properties that are characteristic of RC circuits (circuits having significant resistance and capacitance elements), and the charge Q used for grain attraction that remains from an initial amount of attraction charge $Q_0$ on a grain or substrate as a function of time can be described by an exponential function $$Q=Q_0 e(-kt) \quad (1)$$

having a characteristic time constant k equal to the overall resistance R times the overall capacitance C:

$$k=RC \quad (2)$$

This time constant k is known as an "RC" time constant, and when R and C are expressed in SI units, it has units of seconds. The resistance R is derived from the resistivity by taking into account the cross-sectional area A and length I of the material in question:

$$R=(\rho l)/A \quad (3)$$

where $\rho$ is the bulk resistivity or the equivalent, expressed in standard SI units of ohm-meters.

With prior bead transporter chucks and operation techniques, the resistivity $\rho$ often has to be in excess of $1.1\times10^{11}$ $\Omega$-cm in order to have a time constant—that is, a time in which most grain attraction and deposition must occur (see definition below)—on the order of seconds or more. This problem is particularly acute when dealing with certain edible substrates, such as polyvinylacetate or hydroxypropylmethylcellulose which can have bulk or equivalent surface resistivities $\rho$ well below $10^{11}$ $\Omega$-cm, where the resultant time constant is on the order of tens of milliseconds, which is usually not enough time to accelerate, transport, attract and retain beads.

The result of such low time constants is that because of the internal charge movement and leakage, fewer grains than desired, or no grains, are attracted to intended bead collection zones and/or substrates during bead transporter chuck operation. During synthesis or analysis, instead of retaining a precise amount of ingredients carried by graiss into each bead collection zone or substrate, little or no grain content is attracted and retained where desired, when using quasi-static attracting voltages needed for efficient manipulation of the grains.

In seeking to avoid this lack of chuck response by greatly increasing the applied (attraction) voltage, the attraction field can then be then too strong, causing grains to be attracted to unintended or wrong locations on the bead transporter chuck, or wrongly charged grains to be attracted to the bead transporter chuck or substrate. The same problem also makes it difficult or impossible to perform accumulated charge sensing to gauge how much active ingredient has been attracted and retained by the bead transporter chuck.

It is important to note that many electrostatic bead transporter chucks manipulate charged grains by making use of electrostatic image forces. As a charged grain approaches any metal or conductive surface, such as a bead attraction electrode inside the grain dispenser or container, an image charge of opposite polarity will accumulate on that conductive surface. This happens when mobile charge carriers in the conductive surface are attracted by, or repelled by, the grain charge. This movement of charge in the conductive surface in response to a charged grain in the vicinity creates a potent image charge-induced holding force, or electrostatic image force. This electrostatic image force tends to make the grain highly attracted to, and usually later, in tight contact with, the conductive surface. It should be noted that dielectric grains in stationary tight contact with a conductive surface have a tendency to keep their charge for a period of days. With a grain very close to (e.g., contacting) any conductor, the electrostatic image force generated tends to be greater than that due to any applied field used to accelerate the grains toward the bead transporter chuck, and can be on the order of hundreds of times the force due to gravity.

Typically grains to be transported or manipulated are tribo-charged through frictional encounters and collisions, such as rubbing or bumping into surfaces, where charging can occur by charge induction or charge transfer. The particular charge transfer mechanisms used in a tribo-charging process will determine the applied voltages that should be used on a tribo-charging mesh.

Also, grain motions and interactions, or collisions with obstacles—and each other—inside a dispenser or container tend to randomize their motion, and this influences grain transport properties, as grains are accelerated toward intended bead collection zones.

As discussed below, another problem present in quasi-static biasing techniques involves grain deposition sensing, where an accumulated charge sensing method is used. The static nature of the applied potentials used to attract charged grains to the sensing electrode introduces opportunities for various types of noise—such as shot noise, Johnson (1/f) noise, thermal noise, Galvanic noise, and amplifier noise—to destroy the accumulated charge sense information sought for effective and precise grain accumulation or powder deposition monitoring.

Methods for use of bead transporter chucks and acoustic grain dispensers are set forth in Pletcher et al., "Apparatus for electrostatically depositing a medicament powder upon predefined regions of a substrate," U.S. Pat. No. 5,714,007, issued Feb. 3, 1998; Pletcher et al., "Method and apparatus for electrostatically depositing a medicament powder upon predefined regions of a substrate," U.S. application Ser. No. 08/659,501, filed Jun. 6, 1996, now U.S. Pat. No. 6,007,630; Pletcher et al., "Method and apparatus for electrostatically depositing a medicament powder upon predefined regions of a substrate," copending U.S. application Ser. No. 08/733,525, filed Oct. 18, 1996; Pletcher et al., "Apparatus for electrostatically depositing and retaining materials upon a substrate," U.S. Pat. No. 5,669,973, issued Sep. 23, 1997; Datta et al., "Inhaler apparatus with modified surfaces for enhanced release of dry powders," U.S. Pat. No. 5,871,010, issued Feb. 16, 1999; Sun et al., "Acoustic dispenser," U.S. Pat. No. 5,753,302, issued May 19, 1998; Sun et al., "Electrostatic Chucks," U.S. Pat. No. 5,846,595, issued Dec. 8, 1998; Sun et al., "Electrostatic Chucks," U.S. Pat. No. 5,858,099, issued Jan. 12, 1999; Sun, "Chucks and Methods or Positioning Multiple Objects on a Substrate," U.S. Pat. No. 5,788,814, issued Aug. 4, 1998; Loewy et al., "Deposited Reagents for Chemical Processes," U.S. application Ser. No. 08/956,348, filed Oct. 23, 1997, now U.S. Pat. No. 6,004,752; Loewy et al., "Solid Support With Attached Molecules," U.S. application Ser. No. 08/956,737, filed Oct. 23, 1997, now U.S. Pat. No. 6,045,753; Sun, "Bead Transporter Chucks Using Repulsive Field Guidance," co-pending U.S. application Ser. No. 09/026,303, filed Feb. 19, 1998; Sun, "Bead manipulating Chucks with Bead Size Selector,", U.S. application Ser. No. 09/047,631, now U.S. Pat. No. 5,988,432; Sun, "Focused Acoustic Bead Charger/Dispenser for Bead Manipulating Chucks," U.S. application Ser. No. 09/083,487, filed May 22, 1998, pending. Additional instructional information is found in Poliniak et al., "Dry Powder Deposition Apparatus," co-pending U.S. application Ser. No. 09/095,246, filed Jun. 10, 1998, pending; Sun et al., "Apparatus for Clamping a Planar Substrate," co-pending U.S. application Ser. No. 09/095,321, filed Jun. 10, 1998, pending; and "Pharmaceutical Product and Method of Making," co-pending U.S. application Ser. No. 09/095,616, filed Jun. 10, 1998, pending.

It is therefore desirable to lower the resistivity or charge retention requirement for eligible substrates, allowing for acceleration and attraction of grains to intended bead collection zones or substrates using grains or substrates that are otherwise not workable, as discussed above. Preferably, this should be done while providing grain deposition in a preferred direction and location in conjunction with electrostatic image forces.

Moreover, it is also desirable to have a means for dose monitoring, or grain deposition monitoring. This should allow for accumulated charge sensing with precision in knowing how much charge accumulates on individual substrates or at bead collection zones. Specifically, it is desirable to be able to perform accumulated charge sensing while the bead transporter chuck is in operation, in an effective manner, overcoming the deleterious effects of various noise sources that plague quasi-static biasing techniques.

In attracting and manipulating grains, image charges, electric polarization, and grain mass and transport, play a role.

SUMMARY OF THE INVENTION

These problems are addressed by this invention by introducing AC waveform biasing to attract grains on a bead contact surface of a bead transporter chuck. The beads are directed to bead collection zones on the bead contact surface using pulses or other dynamic, non-static bead electrode bias waveforms which may included AC and DC components, and do not have to be periodic.

In one embodiment, a bead transporter chuck using AC waveform biasing for attracting grains to a bead collection zone on a bead contact surface, and for retaining and discharging grains from the bead collection zone, comprises a bead electrode for selectively establishing a grain attracting field to the bead collection zone, with the bead electrode shaped and configured in such a manner so that when an AC waveform potential is applied to it, the grains are influenced by it and guided to selective retention by the bead electrode to the bead collection zone.

The bead transporter chuck can optionally comprise a dielectric positioned between the bead electrode and the bead contact surface. It can also optionally comprise a shield electrode positioned to shape the attractive field initiated by the bead electrode, and/or it can comprise a floating pad electrode, which in one embodiment is positioned between the dielectric and the bead contact surface. The shield electrode can be shaped and configured so as to allow an electric field from the bead electrode to emanate through the bead collection zone. The shield electrode can be, for example, positioned between the dielectric and the bead contact surface, and formed and configured as to surround, but remain electrically isolated from, the floating pad electrode. If desired, a second dielectric may be positioned between the shield electrode and the bead contact surface or between the floating pad electrode and the bead contact surface, or both.

The bead transporter chuck can comprise a charge collector electrode or a coupling capacitor, or both, for monitoring accumulated charge on the bead collection zone of the bead contact surface.

The AC waveform potential used by the bead transporter chuck can be so chosen and configured so as to provide for a repeated attraction potential at the bead collection zone of the bead contact surface, when the bead collection zone is proximate to a material, such as a low resistivity substrate, that has an RC decay of a charge on the material when the repeated attraction potential is applied. The AC waveform potential is configured such that the time average of the grain attraction potential on the bead collection zone whenever the grain attraction potential acts is greater, on average, than that a second grain attraction potential that would be obtained when applying an equivalent time-averaged DC potential corresponding to the AC waveform potential.

The AC waveform potential can also be chosen so as to maximize a grain attraction potential at the bead collection zone of the bead contact surface, wherein an integral of the absolute value of $V_{BCZ}$ with respect to time, between a point A and a point B on the AC waveform, $$\int_A^B |V_{BCZ}| dt \quad (4)$$

is maximized, with the value of the integral being greater than obtained using a second AC waveform potential not so optimized.

The invention also provides for an accumulated charge sensing circuit for a bead transporter chuck having a charge sensing electrode for monitoring accumulated charge on the bead collection zone of the bead contact surface. This charge sensing circuit comprises a sensing capacitor electrically connected between the charge collector electrode and an AC bias source; and an electrometer electrically connected between the AC bias source and the coupling capacitor so as to be able to measure the potential of the sensing capacitor. The accumulated charge sensing circuit can be used in a process to determine when to stop grain accumulation or to monitor accumulation at various regions on a bead transporting chuck so that process adjustments, such as changes in grain-attracting potentials, can be made on-the-fly.

Another embodiment for an accumulated charge sensing circuit comprises a transformer having a primary winding and a secondary winding, the primary and secondary windings each having first and second poles; the charge collector electrode electrically connected to the first pole [BP] of the secondary winding of the transformer; a sensing capacitor connected between a ground and the second pole [CP] of the secondary winding of the transformer; an electrometer electrically connected between the second pole [CP] of the secondary winding of the transformer and the ground; and an AC bias source connected across the first and second poles of the primary winding of the transformer.

Methods are disclosed for using a bead transporter chuck using an AC bias waveform, with steps including some or all of the following:

[a] applying a first potential to the bead electrode of the bead transporter chuck to create a grain attracting field; and

[b] attracting and retaining a grain to the bead collection zone;

[c] reducing the first potential applied to the bead electrode, thereby reducing the grain attracting field sufficiently so as to discharge a grain from the bead collection zone to a desired location;

[d] aligning the bead transporter chuck with the desired location prior to step [c];

[e] using a bead transporter chuck that comprises a shield electrode positioned between the bead electrode and the bead contact surface; the shield electrode shaped and configured to allow beads to be influenced by the bead electrode;

[f] grounding the shield electrode;

[g] applying a second potential of opposite polarity to the first potential of step [a] to the shield electrode during grain discharge.

DEFINITIONS

Figure 1:
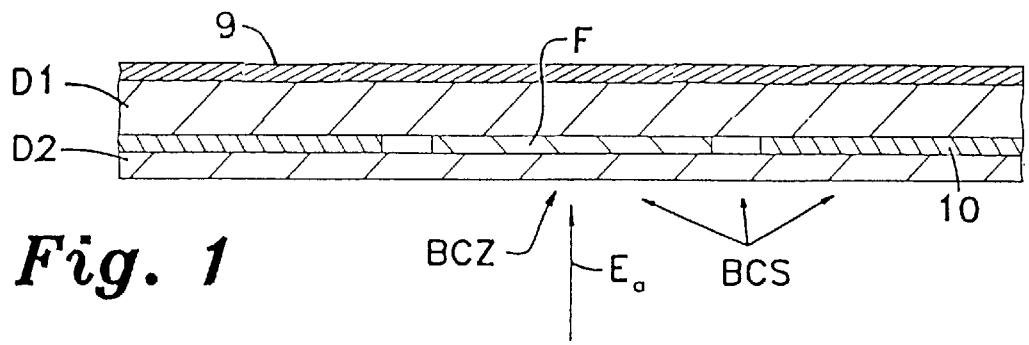
FIG. 1 shows a partial cross-sectional view of a bead transporter chuck that can be controlled using the present invention, with structures shown for one pixel or bead collection zone.

The following definitions shall be employed throughout:

"AC" (alternating current) shall denote any electric current that reverses direction, perhaps periodically; or any applied potential of changing polarity. AC waveforms shall refer to any part or component of such alternating currents, such as a rectified square waveform comprising repeated single polarity pulses (see pulses below), with or without additional DC components.

"Acoustic" can refer to sound waves in air, but more generally may include any alteration of properties of whatever elastic medium is used inside the grain dispenser or grain manipulation theatre. Possible elastic media include dry nitrogen or other gases; water; oil; propylene glycol; refrigerants, such any of the compounds bearing the trademark, Freon® (aliphatic organic compounds containing the elements carbon an fluorene, and others halogens such as chlorine and hydrogen); sand; etc. Properties that may be altered include pressure, particle or molecule displacement, or density. Most commonly, this is achieved using longitudinal compressive waves in the elastic medium, provided by a speaker (see definition below), but it can also occur by using jets or flow of the elastic medium.

"Bead contact surface" shall include all surfaces of the grain manipulating chuck that are accessible to bombardment, contact or exposure to beads, regardless of whether such access is physically encouraged or discouraged. However, when discussing specifically the bead collection zone (see definition below), the bead collection zone can then be considered separately from the remainder of the bead contact surface, to facilitate description of its placement in the grain manipulating chuck. The bead contact surface may be used to retain or accommodate a substrate as discussed herein.

"Bead collection zones" shall include surfaces of the bead contact surface at which grain attracting fields generated by bead electrodes attract and favor retention of a grain. The bead collection zones can be found at holes, apertures, or recessed areas of the bead contact surface, or elsewhere.

"Bead electrode" shall connote any electrode meant to attract and retain materials things such as beads, objects, or particles. It can optionally comprise a hole or aperture through which a grain or object can be viewed. In one embodiment, upon reducing of the electrical potential applied to it, a bead electrode can selectively allow discharge or release of any grain or beads retained.

"Conductor" and "electrode" shall include surfaces or sets of surfaces, continuous or non-continuous, that are capable of carrying electric current. "DC" (direct current) shall denote any quasi-static electric current that flows in one direction only, or any applied potential of single unchanging polarity.

"Dielectric" shall refer to any dielectric material, such as electric insulators in which an electric field can be sustained with a minimum power input; the term is applied generally such that solid metals, if manipulated to meet this definition, for example with a radio frequency applied voltage, can be considered dielectrics. This dielectric material need not be solid (e.g., it can be hollow) and it can be made up of substructures or different constituent dielectric subparts or material types.

"Electrometer" shall connote any voltage measuring device.

"Electronic driver" refers to any power source that can be configured to deliver an appropriate AC waveform potential for operating the bead transporter chucks pursuant to the description herein. The phrase "programmed to deliver the AC waveform potential" does not necessarily imply computer control (though of course computer control is within the invention), since other electrical components can be configured to establish an AC waveform.

"Floating electrode" shall refer to any electrode electrically isolated from ground or other electrodes and capacitively coupled to one or more bead electrodes for the purpose of attracting beads to one or more bead collection zones.

"Grains" are, for the purposes of this application, either aggregates of molecules or particles, typically of at least about 3 nm average diameter, preferably at least about 500 nm or 800 nm average diameter, and, in for example pharmaceutical manufacturing applications, are preferably from about 100 nm to about 5 mm, for example, about 100 nm to about 500 $\mu$m, and are preferably from about 100 nm to about 5 mm, for example, about 100 nm to about 500 $\mu$m. Grains are, for example, particles of a powder. The term "grains" encompasses the term "beads," which refers to any material thing such as a particle, object, tablet or receptacle, capable of being manipulated. This shall include powder, spheres or beads made from polymer and reactive polymer masses, such as styrene-based polymers used in the Merrifield type of solid-phase synthesis. For respiratory administration of medicaments, for example, a 1 to 10 micron range is useful for dry powders, with 4–8 microns preferred.

"Pulse" shall refer to quick variation of applied potentials which are otherwise constant, or nearly constant. This variation shall be of finite duration in relation to the charge decay or charge leakage on a substrate. In shape, a pulse or series of pulses may resemble spikes or parts or components of AC waveforms.

"Reducing," such as in the context of reducing applied potentials to bead electrodes to allow grain discharge, shall include reduction and reversal of polarity of the applied potential, such as going from +500 V to −500 V or vice versa.

"Shield electrode" refers to electrodes that are used at or near the bead contact surface to shield (at least partially) a charged grain from being influenced by attraction fields emanating from a bead collection zone, and/or to define and shape (narrow) the local electric attraction field to encourage grain retention only in intended bead collection zones.

"Speaker" can refer to any loudspeaker, transducer, machine, or device, such as a piezoelectric device, that is capable of providing acoustic energy, such as through pressure modulation; more generally, it is any device capable of altering the properties of the elastic medium used inside the grain dispenser or grain manipulation theatre.

"Substrate" shall refer to any material body that receives or accommodates beads in the course of using a bead transporter chuck. It can comprise, for example, a pharmaceutical dosage form into which active ingredients, in the form of grains, can be attracted and retained. The substrate can be a variety of materials such as an "edible substrate," which is a material which is safe for an animal to consume, for instance because it is metabolized or because it passes through the animal's system without causing any serious problems, or can be something not often considered edible, such as stainless steel. Substrates can be, for example, clamped or placed onto the bead contact surface of a bead transporter chuck, to receive grains in the form of powder, adjacent or over each bead collection zone.

"Time constant" shall refer to the time required for a physical quantity (such as the amount of electrical charge on a substrate) to either rise to $(1-1/e)$ or approximately 63% of its final steady state value, or fall to $(1/e)$ or approximately 37% of its final steady state value, when the physical quantity varies as with time t as $e^{kt}$.

Regarding electrode orientations, the invention is sometimes defined using the terms "around," and "surrounding," such as where a shield electrode 10 surrounds a floating pad electrode F. When electrodes, conductors, or dielectrics are found on different levels or layers of the bead transporter chuck, "around" and "surround" are to be interpreted in view of the areas of the bead contact surface to which the electrode or structure in question will map to by projecting each point to the nearest point on the bead contact surface.

It is also important to note that although the terms electrostatic and quasi-electrostatic are used throughout this disclosure, no limitation is meant or intended in terms of time variations of charge on electrodes and conductors used in the present invention. Electrical currents can and will flow in the course of using the bead manipulating chucks as described, in order to apply and remove electric charge as required, particularly as AC waveforms, pulses, or other dynamic applied potentials are used when using the instant teaching. Although the term, electrical, may also be used in lieu of the term, "electrostatic," a distinction of convenience is made, so as to make clear that while electrical or electrostatic forces are used to attract beads, and the frequency of the applied potentials used is relatively low, that is, not meant to be on the order of radio or microwave frequencies, as discussed below. Potentials refer to electric potentials or applied voltages.

DETAILED DESCRIPTION OF THE INVENTION

Referring to FIG. 1, a partial cross-sectional view of a bead transporter chuck that can be controlled using the present invention is shown, with structures given for one pixel or bead collection zone. The bead transporter chuck shown is merely illustrative, being given by example only to facilitate description. It is one of many typical bead transporter chucks and alternate chuck configurations that can be used to implement this invention.

At the top of this figure, the bead transporter chuck comprises a planar bead electrode 9 that is used to provide a grain attracting field. Affixed to a bottom face of bead electrode 9 is a planar first dielectric layer D1. First dielectric layer D1 is applied to, or has its face affixed to the bead electrode 9 in a parallel plane using any number of techniques known in the art, such as laminating; powder deposition; or thin film deposition, such as magnetron sputtering, or electron beam evaporation. Dielectrics that may be used include commonly available materials such as Corning Pyrex 7740 glass (Corning Inc, Corning, N.Y.); or polyimide resin; a typical thickness is 10–20 mils. Affixed to the other face of first dielectric layer D1 in a similar manner is planar shield electrode 10, which comprises an aperture to accommodate a floating pad electrode F, with the floating pad electrode F coplanar with, and surrounded by shield electrode 10.

Figure 5:
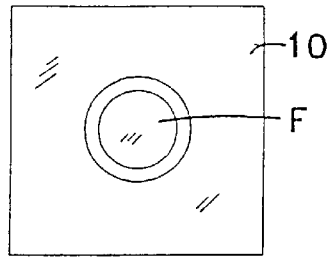
FIG. 5 shows an auxiliary planar view of the bead transporter chuck suggested by FIGS. 1–4, with the view taken in the plane of the floating pad electrode and shield electrode.

Referring now also to FIG. 5, an auxiliary planar view of the bead transporter chuck is shown, with the view taken in the plane of the floating pad electrode and shield electrode. Floating pad electrode F can have a circular shape, as shown, and is also affixed to the other face of first dielectric layer D1. Floating pad electrode F is electrically isolated from the shield electrode 10. This can be accomplished using an air gap, as shown; alternatively, an insulator may be used at the gap to further electrically isolate shield electrode 10 from floating pad electrode F. Affixed in turn to planar shield electrode 10 and floating pad electrode F is a optional planar second dielectric layer D2 shown at the bottom of the chuck structure. Second dielectric layer D2 provides electrical isolation to shield electrode 10 and floating pad electrode F by preventing access to air, where sparks or ionic discharges and breakdowns could occur. It also allows for user safety, isolating the operator from high voltages.

Generally the outer, exposed face of second dielectric layer D2 as shown forms a bead contact surface BCS that is accessible to bombardment, contact or exposure to beads inside a grain dispenser or container, not shown.

Figure 12:
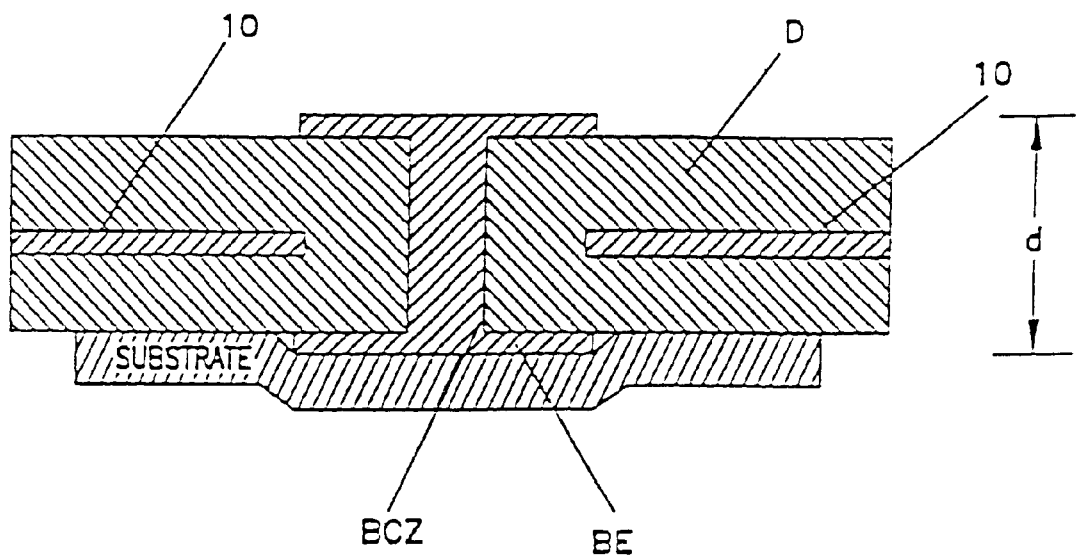
FIG. 12 illustrates how the bead electrode of a bead transporter chuck can contact the substrate and even project out of a dielectric support, where in the illustration a shield electrode is positioned within the dielectric support.

FIG. 12 illustrate features of bead transporter chucks ("electrostatic chucks") at a collection zone that can be favorably employed in the invention. The shield electrode 10 (also termed a "ground electrode" based on a preferred bias) is layered within a dielectric D, which dielectric can be, for example, made of Kapton® (polyimide film, Dupont de Nemours, Wilmington, Del.)(Kapton® can be used as substrate material for Flexible Printed Circuits and can be etched in alkaline solutions, punched and laser drilled, and can be used to form multilayer polyimide film laminates). The grain-attracting electrode or bead electrode BE projects out at the surface that attracts the planar substrate (which is, for example, 1 mil thick) and can project out at the opposing side where electrical contacts are formed. The width of the electrostatic chuck d can be, for example, 0.01 inches. As such, the electrostatic chuck can be relatively flexible. In the illustration, the planar substrate wraps over the outwardly projecting grain-attracting electrode BE in a relatively close-fitting manner.

Generally, to attract and retain beads, the total electrical force $F_{elec}$ generated in the electric field E inside the grain dispenser or container (not shown) on a grain with mass m and charge q must be equal to or greater, overall, than the force $F_{grav}$ of gravity:

$$F_{elec} = Eq \geq F_{grav} = mg \quad (5)$$

Upon applying a voltage to bead electrode 9, a grain attraction field $E_a$ may be established, as shown pointing to the bead contact surface BCS. This attraction field $E_a$ can cause beads to be attracted to and retained by an bead collection zone BCZ, as shown located on the bead contact surface BCS to which the floating pad electrode F projects along its planar axis.

Although the bead collection zone BCZ formed on the exposed portion of second dielectric layer D2 is shown as being flat, it can also be recessed, beveled, bowl-shaped, or have any other profile that can facilitate grain attraction, retention, and discharge, particularly if attributes such as grain size selectivity are sought.

Electric fields, namely $E_a$, in this and later figures are shown using the reverse of the standard convention, showing roughly the direction of the force on a negative test charge. This is because actual examples of applied voltages and grain charges in this disclosure use a working convention that negatively charged beads are to be attracted and, in some cases, later discharged. When manipulating positively charged beads, however, one can simply reverse the applied voltages from those given in the discussion below.

As shown, bead electrode 9 is not exposed to the bead contact surface BCS or the bead collection zone BCZ. The electric field, however, generated by a potential applied to bead electrode 9 can emanate through first dielectric layer D1 (and later through second dielectric layer D2), with the net electric field in the dielectric diminished by electric polarization, depending on its dielectric constant $\epsilon$, which can be anisotropic. See *Classical Electrodynamics 2nd Ed.*, John David Jackson, ©1975, John Wiley & Sons, New York.

A voltage can be applied to bead electrode 9 relative to shield electrode 10 or relative to another surface in the grain dispenser or container to allow attraction of beads to the bead collection zone BCZ. Bead electrode 9 can serve to provide an attraction field for one, or for a plurality, of bead collection zones. Shield electrode 10 may have any other potential applied to it, but it is typically held at ground potential (zero volts) or repulsive potential with respect to the beads to be manipulated.

To aid in visual confirmation of grain capture at the bead collection zone BCZ, a hole (not shown) can be provided through any of bead electrode 9, first dielectric layer D1, floating pad electrode F, and second dielectric layer D2. Such a hole provides a visual or optical monitor sight to verify if a grain is being retained. This allows for automated verification of grain occupancy in the bead collection zone, using known sensors to determine the hole opacity in terms of percent light transmission. For example, the light transmitted through such a hole can be optically mapped onto an array detector such as a charge-coupled device (CCD), an intensified CCD array, a focal plane array, or photodiode array. The array detector can be, for example, a CCD (such as that available from DALSA, Inc. (Easton Conn.), David Sarnoff Research Center (Princeton N.J.) or Princeton Instruments (Trenton N.J.); an intensified CCD array (such as that available from Princeton Instruments, Hamamatsu Corp. (Bridgewater, N.J.) or Photometrics Ltd. of Tucson, Ark.); a focal plane array (such as that available from Scientific Imaging Technologies, Inc. (Beaverton, Oreg.), Eastman Kodak Co., Inc. (Rochester N.Y.) or David Sarnoff Research Center); a photodiode array (such as that available from Reticon Corp. (Sunnyvale Calif.), Sensors Unlimited, Inc. (Princeton N.J.) or Hamamatsu); or a photodetector array (such as that available from FLIR Systems Inc. (Portland Oreg.), Loral Corp. (New York N.Y.) or Hughes Electronic Corp. (Los Angeles Calif.)).

When grounded or biased to a polarity similar to the grains to be manipulated, shield electrode 10 can discourage grains from being attracted or retained at any locations on the bead contact surface BCS other than the intended bead collection zone BCZ. However, shield electrode 10 can comprise any nonconductive material such as an insulator or dielectric.

In lieu of dielectric layers D1 and D2, air or the ambient gas or vacuum can be used as a dielectric or insulator. In this case, insulated mechanical standoffs or other fasteners can be used to hold bead electrode 9 in the same plane as, but offset from, shield electrode 10 and floating pad electrode F. This can expose any of bead electrode 9, floating pad electrode F, and shield electrode 10 directly to the bead contact surface.

Although the bead transporter chuck shown in FIG. 1 is given by way of example only, it should be said that fabrication techniques for forming its conductive layers and electrodes can vary considerably, as any known technique satisfying modest electrical and mechanical requirements can be used. Nearly any metal can be used, for example, to form electrodes 9, F, and 10, which can individually comprise thermally or electromagnetically deposited metals such as indium tin oxide, brass, platinum, copper, or gold, of any useful thickness, but preferably about 1000 Angstroms to 10 microns (100,000 Angstroms). The same is true for dielectric layers D1 and D2—the materials used can be of any type compatible with surrounding electrodes, and having sufficient dielectric strength to withstand anticipated voltages applied, including ceramic materials; silicon dioxide; alumina; polyimide resins and sheets or other suitable polymers; metallic oxides, such as aluminum oxide and titanium oxide; and titanates of calcium and magnesium. Dielectric layers D1 and D2 can, for example, range in thickness from ten Angstroms to 1000 microns. The various layers can be assembled, if desired, using well known adhesives or deposition techniques.

Without being limited to theory, the discussion below sets forth an understanding of theory on how some of the bead transporter (electrostatic) chucks of the invention function. I should be understood that the bead transporter chucks function, and function under the AC electrical driving protocols described herein, regardless of the accuracy of the understandings set forth herein.

Figure 2:
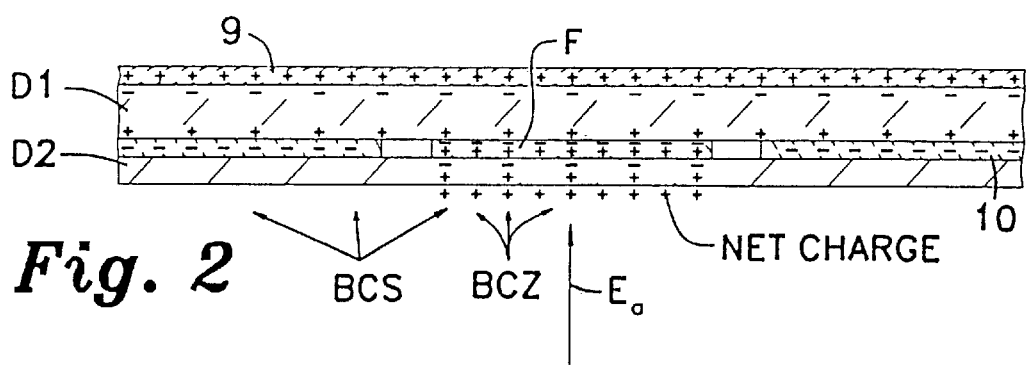
FIG. 2 shows the partial cross-sectional view of the bead transporter chuck of FIG. 1, with an attraction bias applied to the bead electrode, and with resultant symbolic electrical charges shown.

Now referring to FIG. 2, a partial cross-sectional view of the bead transporter chuck of FIG. 1 is shown. Now, however, an attraction bias is applied to the bead electrode 9, and shield electrode 10 is grounded (zero volts). Resultant symbolic electrical charges are as shown. Using a wire, conductor, cable, via, or bus (not shown), a positive potential is applied to bead electrode 9 as shown, so as to attract and retain negatively charged beads. This positive potential on bead electrode 9 is shown using a full row of positive symbols to indicate a positive net charge there. This positive charge creates an electric field which emanates through space, including downward on the page toward first dielectric layer D1 (field lines omitted). As this positive electric field traverses first dielectric layer D1, polarization in dielectric layer D1 results in charge shifting, forming a certain induced electric dipole moment per unit volume. This induced electric dipole moment per unit volume is electrically equivalent to induced surface charge per unit area, appearing on both planar faces of first dielectric layer D1. This polarization cancels some, but not all, of the electric field due to the potential applied to bead electrode 9, and this polarization is shown as a half-seeded row of negative and positive surface charges as shown at the planar faces of first dielectric layer D1. This forms a series of electric dipoles—positive and negative charges separated by a distance—that, shown here for illustration, cancel half the electric field inside first dielectric layer D1. For illustration purposes, this corresponds to a dielectric constant $\epsilon=2$ (exactly) for first dielectric layer D1.

The electric field experienced by the shield electrode 10, however, is in effect, governed by the laws of capacitors (see ref: *Physics,* 3rd Edition, by David Halliday and Robert Resnick, John Wiley & Sons, NY, ©1978). Bead electrode 9 and shield electrode 10 as shown form a capacitor, with their mutual dielectric being dielectric layer D1. Accordingly, shield electrode 10 experiences a corresponding full negative charge, represented by the single full row of negative symbols. The result is that the projection of shield electrode 10 onto the bead contact surface BCS is field-free, that is the electric field is essentially zero, ignoring minor fringe effects. In this sense, the shield electrode 10 acts as a Faraday shield, preventing any electric field from emanating through it to the bead contact surface.

The situation is different, however, in the vicinity of the floating pad electrode F. Not connected to ground, and uncharged initially, the floating pad electrode F can only rearrange its charges, and cannot sustain or have a net charge as do the bead electrode 9 and shield electrode 10 in this example. Furthermore, also being a conductor, charges in floating pad electrode F are free to move, not limited to simple charge shifting exhibited during polarization. But like the shield electrode 10 above, the floating pad electrode F also forms a capacitor with bead electrode 9, with first dielectric layer D1 as their mutual dielectric. As a result, charges in electrode F move internally along its planar axis, and the planar surface that floating pad electrode F shares with the first dielectric layer D1 displays a full set of negative charges as shown. But since the net charge on floating pad electrode F must be zero—it is electrically isolated—a full set of positive charges form on the planar surface of floating pad electrode F that it shares with the second dielectric layer D2.

Underneath, second dielectric layer D2 on its face shared with the floating pad electrode F as shown, the net charge seen by the dielectric D2 is a full row of positive charges, just as the first dielectric layer D1 above saw a field consisting of a full row of positive charges. This can be verified by canceling charges as shown. The result is again polarization in second dielectric layer D2 in a manner similar to that described above for first dielectric layer D1.

In the vicinity of the bead collection zone BCZ, the electric fields created thus far add up to an unbalanced or net charge (NET CHARGE), a full row of positive charges, as shown. This net charge is the charge that is in theory available on the bead collection zone BCZ to attract negatively charged beads and powders, and the electric attraction field it creates is represented by the attraction field $E_a$ as shown. Once enough negatively charged grain material lands and is retained on the bead collection zone BCZ, the available net or unbalanced charge goes to zero, and deposition usually ceases, unless beads in the vicinity are overcome by electrostatic image forces (see above).

Figure 3:
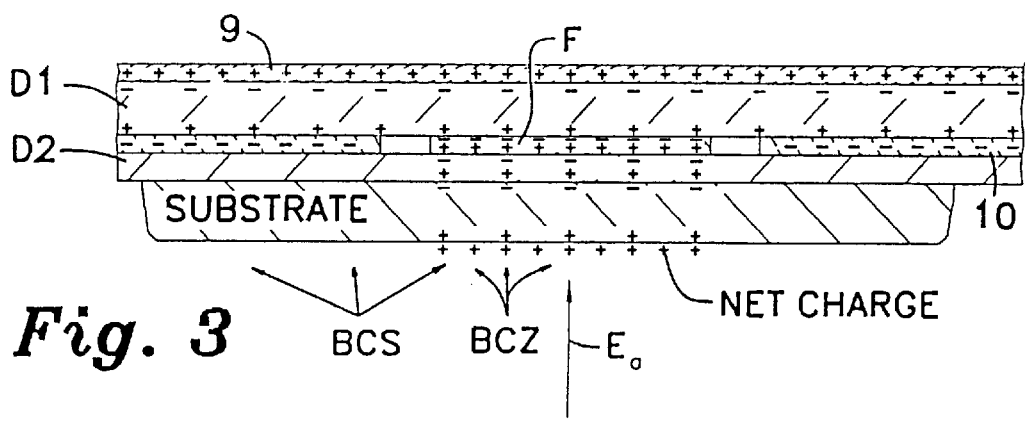
FIG. 3 shows the partial cross-sectional view of FIG. 2, with a high-resistivity substrate contacting or clamped to the bead transporter chuck so that it can receive grain deposition, and with resultant symbolic electrical charges shown.

Now referring to FIG. 3, a partial cross-sectional view as shown in FIG. 2 is given, with a high-resistivity substrate (shown as SUBSTRATE) added to the second dielectric layer D2 by contacting or being clamped to the bead transporter chuck so that it can receive grain deposition, such as during preparation of drug administration forms. Resultant symbolic electrical charges are again shown. For the components repeated here, the electrical behavior and arrangement of charges is as given above for FIG. 2, but now a relatively high resistivity ($\rho=10^{15}$ Ω-cm, for example) substrate (SUBSTRATE) is added, firmly contacting the former bead contact surface BCS on second dielectric layer D2 as shown on FIG. 2. In this case, the unbalanced net charge (NET CHARGE) which was available for grain attraction is now affected by the dielectric properties of the substrate. Thus, polarization again occurs (shown here symbolically for illustrative purposes are the effects of a dielectric material of dielectric constant $\epsilon=2$), with separated half-seeded charges shown as done above for dielectric layers D1 and D2.

For a high resistivity substrate, the charge retention is good as a function of time, being more or less constant, that is, the RC time constant is on the order of many minutes or hours, giving ample time for the grain deposition process. Once again, the electric fields created thus far, including now the substrate (SUBSTRATE), add up to an unbalanced or net charge (NET CHARGE), a full row of positive charges, as shown on the exposed portion of the substrate. This net or unbalanced charge on the substrate surface creates a new bead collection zone BCZ. This net charge at the bead collection zone BCZ is available to attract negatively charged grains such as powders. The electric field it creates is again represented by the attraction field $E_a$ as shown. Once enough negatively charged grain material lands and is retained on the new bead collection zone BCZ on the substrate surface, the available net or unbalanced charge—and the resultant electric field or voltage on the bead collection zone BCZ—go to zero, and deposition is no longer explicitly encouraged.

Figure 4:
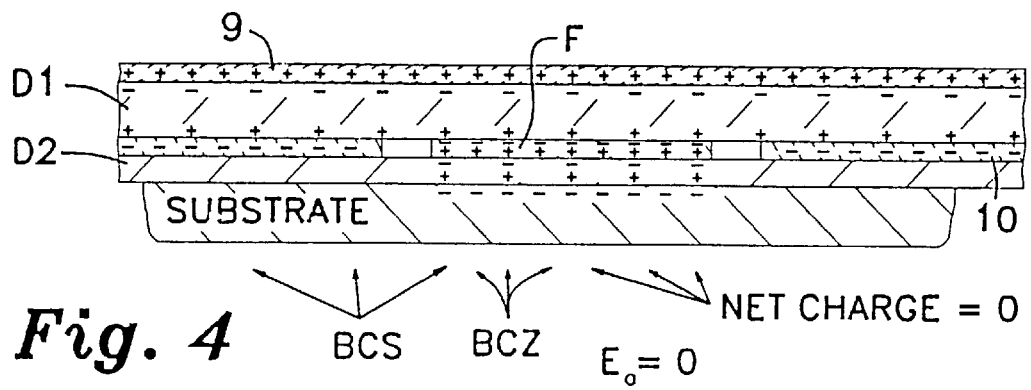
FIG. 4 shows the partial cross-sectional view of FIG. 3, with a low-resistivity substrate contacting or clamped to the bead transporter chuck so that it can receive grain deposition, and with resultant symbolic electrical charges shown.

Now referring to FIG. 4, another partial cross-sectional view is given reproducing the elements shown in FIG. 3, but now SUBSTRATE is a low-resistivity substrate (e.g., $\rho=10^{11}$ Ω-cm) contacting or clamped to the bead transporter chuck, and some time greater than a few time constants has passed.

The lower resistivity substrate (SUBSTRATE) no longer acts as a dielectric. The resistivity is low enough that the RC time constant as mentioned above is on the order of milliseconds. After a few time constants have passed—generally not enough time for grain attraction or deposition—the substrate undergoes internal flow or movement of charges that leak out or cancel the unbalanced or net charge (NET CHARGE) shown in FIG. 3. In this substrate as shown, negatively charged carriers have not simply shifted, but have moved, macroscopically through the substrate. These negative charges in the substrate cancel the net charge that would have accrued on the surface, as shown in FIG. 3. Humidity and airborne dust can play a role in this process, helping to dissipate induced charge on the substrate. This stray environmental dissipation of charge allows that the substrate does not necessarily have to become or remain positively charged overall for very long for this to happen. With no remaining net or unbalanced charge left over at the bead collection zone BCZ on the substrate surface, no potential or voltage exists to move or accelerate grains. The grain attraction field $E_a$ becomes zero, as shown.

This can be seen visually, using the symbolic charges, by counting charges and cancelling. Certain compensating positive charges that may reside at edges of the substrate are not shown for clarity.

Figure 6:
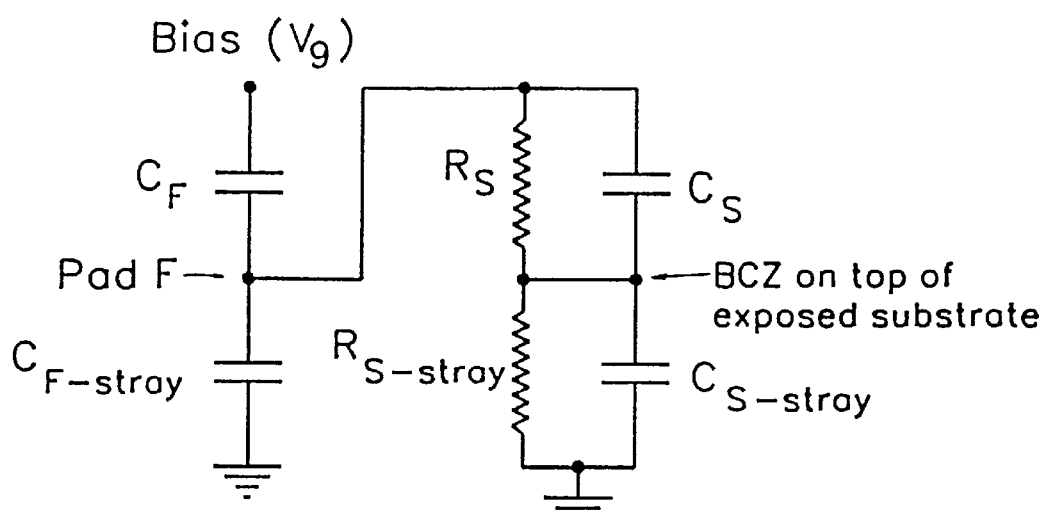
FIG. 6 shows an equivalent circuit that can represent the electrical behavior of the bead transporter chuck of FIGS. 3 and 4.

Referring to FIG. 6, an equivalent circuit is shown that can schematically represent the electrical behavior of the bead transporter chuck of FIGS. 3 and 4. It shows main influences in terms of capacitances and resistances and serves as an illustration only. The applied voltage or bias on bead electrode 9 is shown as Bias ($V_9$), originating from a power source, not shown. Bias V9 is applied across a capacitance CF comprising first dielectric layer D1 to floating pad electrode F, shown as Pad F. Pad F is in turn affected by stray capacitance $C_{F\text{-}stray}$, forming a equivalent capacitor with the shield electrode 10 and possibly the ambient air or fluid inside the chuck, depending on its construction.

Floating pad electrode F in turn is coupled to another charge transferring element—the bead collection zone BCZ at the exposed surface of the substrate (shown as BCZ on top of exposed substrate). Significant elements here include resistance. Floating pad electrode F acts as a capacitor with the bead collection zone BCZ, with the second dielectric layer D2 as the dielectric, with an equivalent capacitance shown as $C_S$. This coupling between floating pad electrode F and the bead collection zone BCZ also has a resistance $R_S$ associated with it, mostly from resistivity of the substrate itself, that is, for charges to migrate to the exposed substrate surface.

Finally, the bead collection zone BCZ on the exposed substrate is capacitively coupled to ground—via the shield electrode 10, the substrate, and through humidity and other local environmental factors. The equivalent capacitance is shown as $C_{S\text{-}stray}$. $C_{S\text{-}stray}$ derives its value from the capacitance of second dielectric layer D2, the substrate, and from local environmental factors, like dust and humidity. The coupling between the bead collection zone BCZ and ground also has a resistance $R_{S\text{-}stray}$ associated with it as shown, mostly from resistivity of the substrate itself and that of second dielectric layer D2.

Figure 7:
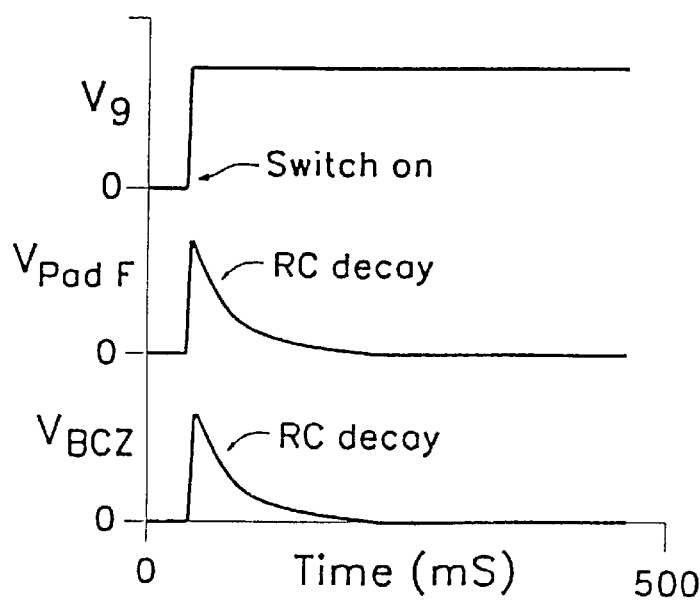
FIG. 7 shows three cartesian graphical waveforms representing applied and resultant voltages in the bead transporter chuck as a function of time, where a low-resistivity substrate is applied thereto, and using quasi-static biasing.

Now referring to FIG. 7, three Cartesian graphical waveforms are shown to represent applied and resultant voltages in the bead transporter chuck as a function of time, where a low-resistivity substrate is applied thereto (as in FIG. 4), and using traditional quasi-static biasing. The voltage versus time waveform labeled $V_9$ represents the voltage applied to the bead electrode 9. As shown, after approximately 40 mS, the voltage is switched on, and remains at some desired level in an attempt to induce grain attraction and retention.

The voltage versus time waveform labeled $V_{BCZ}$ represents the voltage or electric potential, grain attraction potential, that exists on the bead collection zone BCZ on the exposed portion of the substrate. In this case, it is the amount of charge that is retained—that is, undistributed, not leaked away—on the surface of the substrate at the bead collection zone BCZ, such as that shown at the bottom of FIG. 3—that determines the voltage $V_{bcz}$. This unbalanced charge is what helps determine the resultant potential voltage on the floating pad electrode F, shown in the waveform labeled $V_{Pad\ F}$.

No grain or powder deposition is shown or demonstrated in these voltage curves. Upon application of the bias potential to bead electrode 9, shown by the steady high state value in $V_9$, both $V_{Pad\ F}$ and $V_{BCZ}$ shoot up to high state values, representing a full unbalanced charge present at the bead collection zone BCZ and therefore the floating pad electrode F. Then, both potentials $V_{Pad\ F}$ and $V_{BCZ}$ undergo a characteristic RC time constant decay. This is due directly to the currents or motion of charge carriers in the substrate responding to the applied field at bead electrode 9. The charge rearrangement in the low resistivity substrate leaks off the unbalanced charge on the bead collection zone BCZ on the substrate surface. After one characteristic time constant, both potentials $V_{Pad\ F}$ and $V_{BCZ}$ fall to about (1/e), or approximately 37% of their final steady state values. This means that only 37% of the initial charge present on the bead collection zone BCZ of the substrate surface remains. Often, within milliseconds, the charge Q remaining goes to virtually zero, and the bead transporter chuck stops working.

Figure 8:
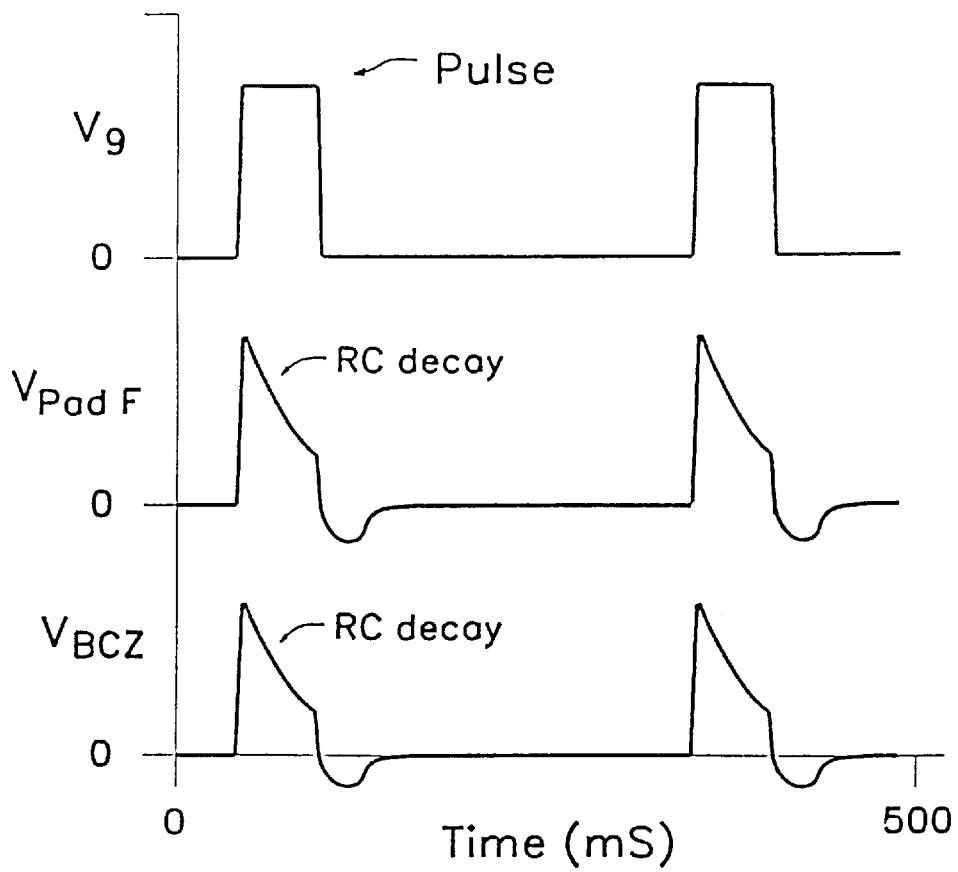
FIG. 8 shows three cartesian graphical waveforms representing applied and resultant voltages in the bead transporter chuck as a function of time, where a low-resistivity substrate is applied thereto, and using AC waveforms biasing.

Referring now to FIG. 8, three Cartesian graphical waveforms are shown representing the same applied and resultant potentials in the bead transporter chuck as given in FIG. 7, but where the problem of attracting beads to low resistivity substrates is solved, using AC waveforms biasing at the bead electrode 9. As shown, bead electrode 9 bias $V_9$ comprises a single polarity pulse of limited duration, about 40 mS. The pulse, labeled Pulse is approximately a square wave, and can have, for example, a peak value of 2000 volts positive, for attraction of negative beads. During the high state value of the pulse, the profile of $V_{Pad\ F}$ and $V_{BCZ}$ are as before in FIG. 7—charge on the bead collection zone BCZ and floating pad electrode F is built up quickly to a maximum value, then immediately starts leaking away, as discussed above.

However, just as much of the charge on the bead collection zone BCZ has leaked away, the Pulse bias $V_9$ is brought back to zero, as shown. $V_{Pad\ F}$ and $V_{BCZ}$ then relax, decreasing rapidly and then perhaps overshooting somewhat, and switching polarity because of opposite-polarity leakage charges that remain close to the bead collection zone BCZ and have not yet moved back to their former positions. After an interval—and this temporal spacing is determined by the relevant time constants involved—the offending leakage charge carriers have dissipated, and the bias pulse $V_9$ is then administered again, as shown. These periodic waveforms provide momentary impulses that allow grain attraction to take place even though the charge leakage in and across the substrate is substantial. These single polarity periodic pulses may be generated by known power supplies, including those using step-up transformers so that AC bias waveforms with voltages in the kV range may be generated by simple inexpensive power supplies at much lower voltages. This is possible because the actual high voltage current flow into the chuck can be as low as the nano-Ampere range.

With the aid of the electrostatic image force on charged beads, this technique has been found to work for low resistivity substrates of $\rho=10^{10}$ Ω-cm, and perhaps lower. The frequency of single polarity periodic pulses must be low enough, however, for the beads to respond. Essentially, the attractive field $E_a$ provided by providing AC biasing at the bead electrode 9 must act long enough temporally to have the beads experience an attractive force for some time and have a chance to accelerate by overcoming inertia and collisions with other beads. If the frequency of the periodic waveform at $V_9$ is too high, the applied voltage operatively takes on attributes of quasi-static biasing, and the time-averaged leakage current becomes more effective in draining the net charge on the bead collection zone.

There is a broad range of possible bias waveforms and of workable frequencies, and empirically-based adjustments can provide a good source of values for optimal frequencies. For example, a single polarity periodic set of square wave pulses, of frequency of about 4 Hertz, and peak voltage value durations of about 40 mS works well. It has also been discovered that grain powder charged to 10 mC/g will respond to periodic pulses of up to 100 Hertz frequency. This technique also allows satisfactory operation of bead transporter chucks at high relative humidity, such as 50–60% humidity. Active ingredient dosage deposits ranging from 300–800 micrograms are obtained (e.g., on 4 mm diameter collection zones), on low resistivity substrates where higher amount depositions were previously difficult.

Even on higher resistivity substrates having an RC time constant on the order of minutes or hours, AC waveform biasing can help to mitigate the action of residual surface charges that migrate and help dissipate the net charge used to attract beads at the bead contact surface.

Figure 9:
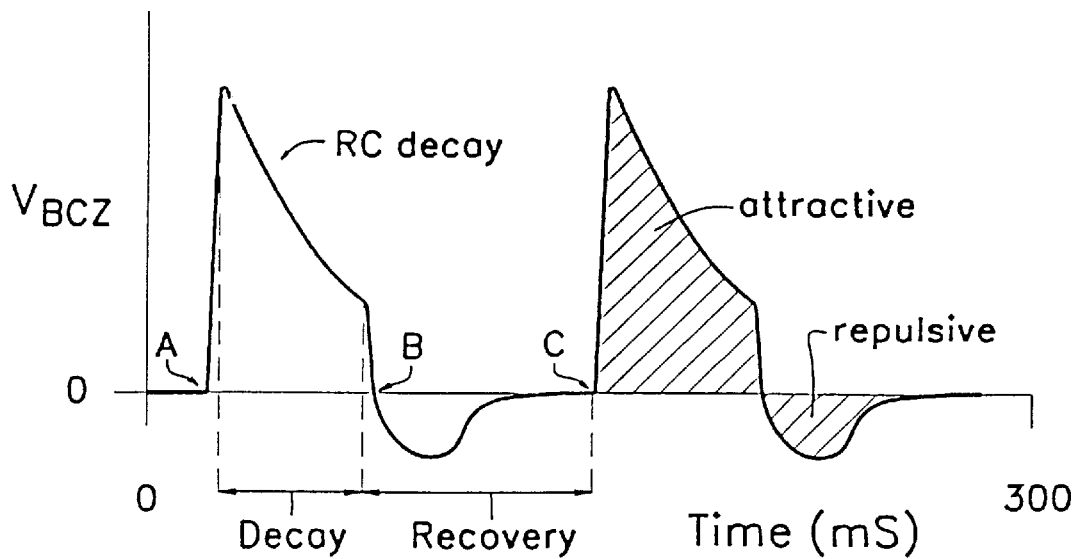
FIG. 9 shows a cartesian graphical waveform representing a resultant voltage at the bead collection zone in the bead transporter chuck as a function of time, where a low-resistivity substrate is applied thereto, and using AC waveforms biasing.

Referring now to FIG. 9, the necessary attributes of an effective AC bias periodic potential or waveform can be illustrated, using the example of a single polarity square waveform from FIG. 8. FIG. 9 gives another cartesian graphical waveform representing the potential at the bead collection zone BCZ as a function of time, shown magnified with respect to the previous figure. It shows the grain attraction potential $V_{BCZ}$ on the substrate that results from the pulse waveform shown in FIG. 8, except that the square wave pulses delivered to the bead electrode 9 (shown as $V_9$) occur more frequently, with less temporal spacing.

Starting at point A as shown, the potential $V_{BCZ}$ on the substrate surface rises rapidly in response to the single polarity square wave pulse ($V_9$) delivered to bead electrode 9. As before, leakage processes cause unwanted charge cancellation at the substrate surface, and a characteristic RC decay of the potential $V_{BCZ}$ occurs. This is shown labeled Decay. During the next phase, the applied square wave potential $V_9$ drops to zero, and a recovery phase, labeled Recovery, begins. During recovery, the potential $V_9$ is zero or can simply have some lower value than its peak value. In this example, $V_9$ goes to zero, and in the initial part of the recovery phase, $V_{BCZ}$ in turn goes to zero. Then because of charge leakage in the reverse direction that has not yet completely occurred to bring about a return to equilibrium, $V_{BCZ}$ can momentarily overshoot and go negative, as shown between points labeled B and C.

So long as $V_{BCZ}$ is positive, such as shown between points A and B, grain attraction can take place. This part of the potential wave for $V_{BCZ}$ is labeled attractive. When $V_{BCZ}$ reverses polarity momentarily during the recovery phase, as shown between points B and C, the bead collection zone BCZ on the substrate or bead contact surface becomes repulsive (typically mildly repulsive) to properly charged beads; this is shown labeled repulsive.

The pulses of the AC bias waveform for $V_9$ can be put close together, so as to place the potential waves for $V_{BCZ}$ close together as shown, minimizing the time when $V_{BCZ}$ is zero or close to zero. This improves the time-averaged characteristics of the potential at the bead collection zone BCZ.

The possible AC biased waveforms $V_9$ that may be applied to the bead electrode 9 can vary widely in character. The AC bias applied may comprise a mixture of AC and DC components and may be mixed, comprising square wave, sinusoidal, saw tooth, and other waveforms and their mixtures. For example, the waveform given here can be added to a fixed DC potential of, say 200 volts, elevating the pulsed waveforms.

The AC bias voltage pattern chosen for $V_9$ should preferably be chosen to maximize the time averaged or cumulative potential at the bead collection zone BCZ during a single periodic repetition of the waveform, or, if the waveform is aperiodic, during the time needed for grain attraction. This may be achieved for this example by choosing a $V_9$ waveform that maximizes the integral of the absolute value of $V_{BCZ}$ with respect to time, between points A and B, that is, maximize $$\int_A^B |V_{BCZ}| dt \quad (6)$$

where A and B are time values at points A and B on FIG. 9. In a similar manner, if a given AC bias $V_9$ waveform produces significant repulsive behavior during the recovery phase, one can choose or alter a $V_9$ waveform that minimizes the integral of $V_{BCZ}$ with respect to time, between points B and C, that is, minimize $$\int_B^C |V_{BCZ}| dt \quad (7)$$

where B and C are time values at points B and C on FIG. 9. For particularly effective time-averaged values of $V_{BCZ}$ that provide maximum motive force for beads that need to overcome collisions and other obstacles, one can instead choose AC bias $V_9$ waveforms that maximize $V_{BCZ}$ raised to some positive power greater than one, such as maximizing its square over the time interval from point A to point B, that is, by maximizing $$\int_A^B (V_{BCZ})^{*2} dt \quad (8)$$

which would encourage temporal emphasis on high values of $V_{BCZ}$ by weighting the average in favor of values of $V_{BCZ}$ that are close to peak or maximum.

This optimizing of the $V_9$ waveform functionality for a given chuck can be calculated beforehand, even without much empirical study, by empirically measuring values for the resistances and capacitances, that is, $C_F$, $C_{F-stray}$, $C_S$, $R_S$, $C_{S-stray}$, and $R_{S-stray}$, of the equivalent circuit discussed in FIG. 6. By using known equations for the circuit as shown, or any other equivalent circuit that applies to the bead transporter chuck in question, one can use computer optimization or other numerical techniques to calculate what form the potential $V_{BCZ}$ takes upon stimulation by any proposed $V_9$ waveform.

In any case, the AC waveform bias or potential $V_9$ will be chosen so that the time average of the grain attraction potential $V_{BCZ}$ that results on the bead collection zone is greater, on average, than that that would be obtained when applying an equivalent time-averaged DC potential $V_{9-DC}$—perfectly rectified and smoothed—that corresponds to the AC waveform potential $V_9$ at the bead electrode 9. With $V_{BCZ}$ obtained using the AC waveform potential $V_9$, we can use the name $V_{BCZ-DC}$ for the grain attraction potential that results from using the time-averaged DC potential $V_{9-DC}$. That is:

$V_{BCZ}$ results from use of AC bias potential $V_9$, $V_{BCZ-DC}$ results from use of DC equivalent bias $V_{9-DC}$.

The time-averaged DC potential $V_{9-DC}$ can be calculated by time-averaging the AC waveform bias $V_9$ by taking the integral of $V_9$ divided by time t, with respect to time:

$$V_{9-DC} = \int_A^B V_9/t dt \quad (9)$$

For example, if a square wave is used for $V_9$ that consists of 1000 volt peaks that occur 50% of the time, but is zero at other times, the equivalent time-averaged DC potential $V_{9-DC}$ will be equal to 500 volts. The grain attraction potential $V_{BCZ}$, on average, that results from using the 1000 volt AC waveform peaks will be greater than that obtained by applying a plain 500 volts DC to bead electrode 9.

This means that the integral of the absolute value of $V_{BCZ}$ over the attraction phase from point A to point B, divided by time t, is greater than the integral of $V_{BCZ-DC}$ obtained when using the equivalent time-averaged DC potential, $V_{9-DC}$ at the bead electrode 9, or $$\int_A^B |V_{BCZ}|/t dt > \int_A^B |V_{BCZ-DC}|/t dt \quad (10)$$

Time t shall be chosen to have only positive values.

Even if the $V_9$ waveform chosen for application to the bead electrode 9 results in significant repulsive behavior, grain attraction will still be well served, because the attraction periods in the $V_{BCZ}$ waveform will be more effective than the repulsion periods. This is mostly because of the electrostatic image force that beads will experience upon nearing the chuck, regardless of the actual $V_{BCZ}$.

In the vicinity of the bead transporter chuck, with a charged grain at a distance d from any conductive surface in the chuck, the electrostatic image force, $F_{image}$, due to the image charge can become, as the grain nears the chuck, more significant than the force $F_{elec}$ given above. Roughly, the dependence of the electrostatic image force on the distance d for a given charge q on a grain, is as follows, using Coulomb's Law for stationary point charges:

$$F_{image} = \frac{q^2}{4\pi\varepsilon_0 d^2 (\pi d_{bead}^3/6)\rho \bullet g} \quad (11)$$

In the denominator, $\epsilon_0$ is the vacuum permittivity; $(\pi d^3/6)$ is the grain volume; $\rho$ is the grain mass density in kg/m$^3$; and g is the acceleration due to gravity. This gives the electrostatic image force in units of g. This can become a potent force at short distances, but the grain attraction field $E_a$ is still needed to bring charged beads within its influence.

Other techniques may be used simultaneously to enhance bead transporter chuck effectiveness, including use of periodic air or fluid flow provided acoustically by a conventional speaker. Such a speaker (not shown) can be in fluid communication with some part of the grain dispenser or grain manipulation theatre, so that it may direct acoustic energy to unseat beads that are held by electrostatic image forces to dispenser surfaces, or during grain discharge at a desired target, to unseat grains held by electrostatic image forces to the chuck itself.

The use of AC bias waveforms for the bead electrode 9 also solves another longstanding problem during deposition sensing. During deposition sensing, one or more bead collection zones are closely monitored for grain accumulation, so as to allow regulation of the grain deposition process, to produce for example precise dosages. This can be done optically or by measuring accumulated charge using an "on-board" charge sensor at a sensor-associated bead collection zone, which can be correlated to actual charged grain deposition by empirical data collection. In dry powder deposition, for example, dose monitoring is often a very difficult task, particular for dosages below one milligram.

The difficulty is not that measuring devices are not available—modern solid state devices, although expensive, can make measurements so precise that noise levels are on the order of the voltage generated by the charge of a few hundred electrons. Rather, the difficulty lies with various practical and environmental factors that can deteriorate charge sensing sensitivity by two or three orders of magnitude. For quasi-static DC biased bead transporter chucks, on-board charge sensing is particularly difficult. Data obtained by depositing on a polypropylene film substrate with different potentials indicates that the deposited dose is linearly related to the bias potential if that potential is above a certain threshold potential. Data indicates that threshold potential is about 100–200 volts DC, at least for certain transporter chucks.

Figure 10:
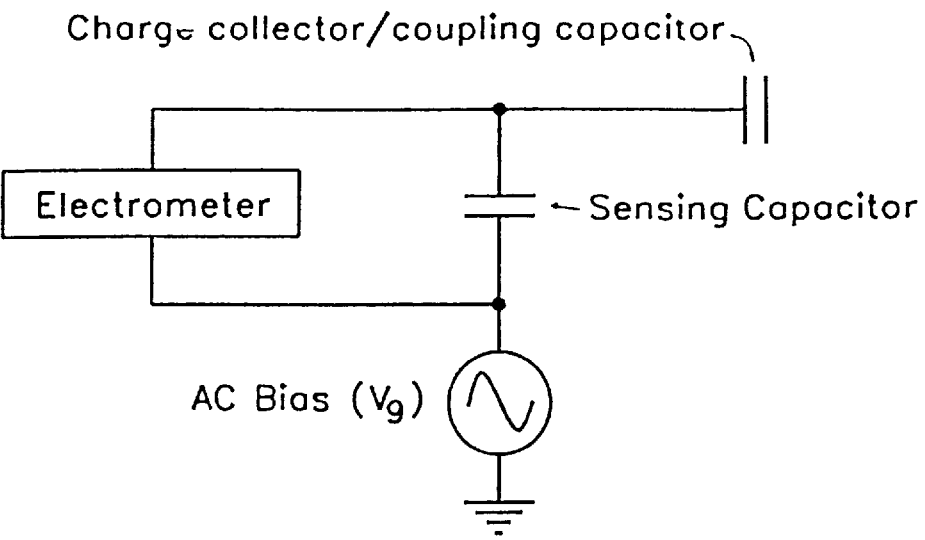
FIG. 10 shows one possible equivalent circuit diagram that provides AC biased charge and deposition sensing for at least one of the bead collection zones of the bead transporter chuck shown in FIGS. 1–4.

Referring now to FIG. 10, one possible equivalent circuit diagram that provides AC biased charge and deposition sensing for at least one of the bead collection zones of the bead transporter chuck shown in FIGS. 1–4 is shown. One or more bead collection zones BCZ are typically dedicated solely for sensing or are in general use, but closely monitored. By measuring the lowering of the attraction potential $V_{BCZ}$ that occurs as charged beads deposit on the bead collection zone, a measure of deposited charge can be obtained, and by knowing the average charge/mass ratio q/m of the deposited grains (e.g., beads or powder), the accumulated grain deposition mass can be measured. One can measure $V_{BCZ}$ directly across a charge collector electrode, but it is often preferable to measure the potential across a coupling capacitor, such as the floating pad electrode F discussed above, whose waveform is shown in FIG. 8. The coupling capacitor as embodied by floating pad electrode F above will provide reasonably high fidelity reproduction of the potential at the bead collection zone BCZ on the bead contact surface, and in FIG. 8 the waveforms for $V_{BCZ}$ and $V_{Pad\ F}$ reflect this. In either case, whether a charge collector or charge coupling capacitor is used, they may both be considered charge sensing electrodes, such as in the appended claims. In the equivalent circuit of FIG. 10, the charge collector/coupling capacitor is electrically connected to a separate sensing capacitor. The voltage generated across the sensing capacitor can be a reliable indicator of the potential $V_{BCZ}$, and one simply measures the voltage across the sensing capacitor with an electrometer, such as a Keithley model no. 614, 6512, 617, 642, 6512, or 6517A electrometer, as shown schematically in the figure. Generally the coupling capacitor is any electrode that is capacitively coupled to a bead collection zone on the bead contact surface.

A problem is that DC biasing can cause a steady drift in the reading of the potential across the sensing capacitor. This drift comes from many sources, mostly from natural leakage across the dielectric material in the sensing capacitor, and because of charge leakage in the substrate or grain composition on the accumulated on the chuck. Drift can also be induced by noise factors such as shot noise, Johnson (1/f) white noise, thermal noise, Galvanic noise, triboelectric noise, piezoelectric noise, amplifier noise, and electromagnetically induced noise. See ref: *The Art of Electronics,* by Paul Horowitz, Winfield Hill, 2nd Edition, Cambridge University Press, ©1989 ISBN 0521370957, which is incorporated as a reference in its entirety.

If this drift is too large compared to the actual charge collected at the bead collection zone, the accuracy of the charge sensor as a dose or deposition measurement tool can be unacceptably low. Using AC biased waveforms as taught here, however, minimizes the creation of drift, in a manner similar to that used above for avoiding the "drift" of charge dissipation on the bead collection zone, allowing precise measurement of charge collected. As shown on the figure, an AC bias source is shown, and may simply be the same source as discussed above, with the AC bias potential simply applied or administered via the bead electrode 9. This will in turn electrically couple to the floating pad electrode F or to the bead collection zone itself, if one elects to connect it directly to the sensing capacitor as shown.

For example, if the sensing capacitor is chosen to be 0.1 $\mu$F, and the q/m of the powder is 10 $\mu$C/g, a 100 mV signal change on the charge collector/coupling capacitor corresponds to 1 mg of powder deposited on the bead collection zone. If, say, the linear correlation factor is 3, then 1 mg of powder on the sensor corresponds to 3 mg of powder in the actual deposition dose, then a 99 $\mu$g actual dose will have a detectable potential change of 3.3 mV. With a 5% error tolerance, the corresponding background unpredictable noise contribution cannot exceed 160 $\mu$V. This is achievable with careful shielding and grounding design. Preferably the charge collector is integrated with the chuck design to assure a consistent correlation.

In effect, the same benefits gained by using the AC bias waveforms for $V_9$ to avoid charge dissipation in the substrate can be used to greatly reduce drift in the charge sensing circuit, too.

Figure 11:
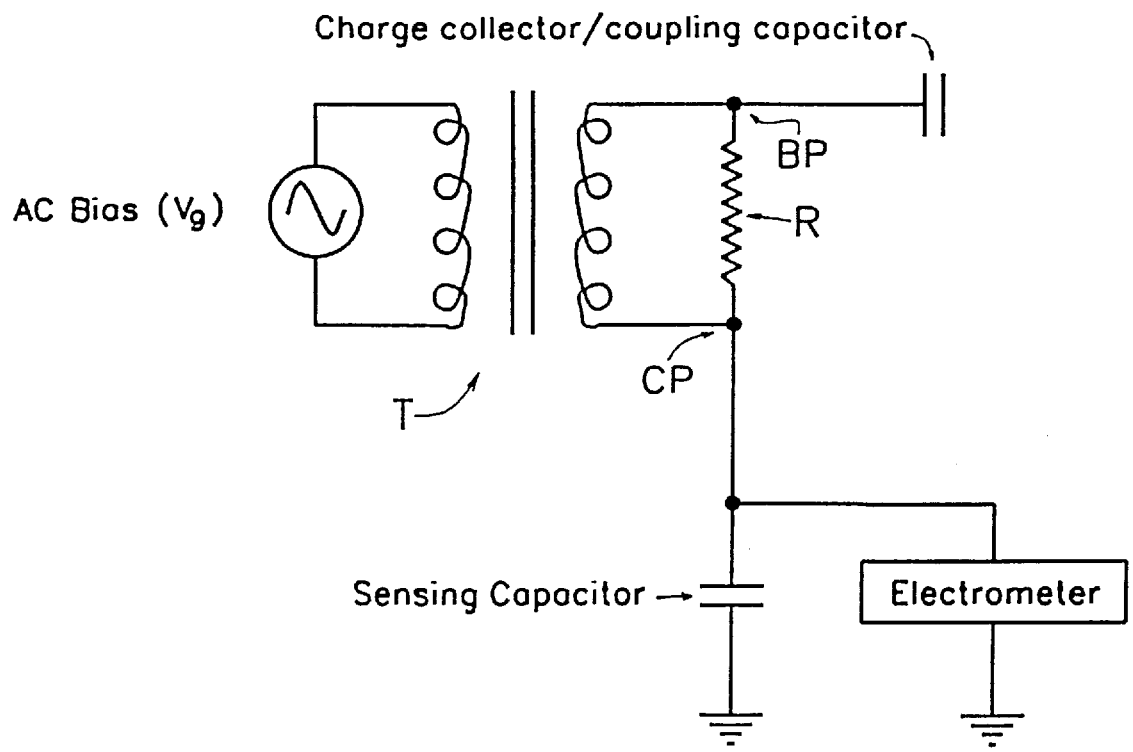
FIG. 11 shows another possible equivalent circuit diagram that provides AC biased charge and deposition sensing for at least one of the bead collection zones of the bead transporter chuck shown in FIGS. 1–4.

Referring now to FIG. 11, another possible equivalent circuit diagram that provides AC biased charge and deposition sensing is shown. This arrangement further reduces noise by separating the AC bias source from the electrometer, the sensing capacitor or the charge collector/coupling capacitor, all components whose sensitivity to noise is critical. As shown in the figure, the AC bias source is connected to the primary of an transformer T. In this manner, only the periodic magnetic field generated by $V_9$, (not $V_9$ itself) is introduced into the sensitive components on the right side of the figure. The secondary winding of transformer T is connected across a stabilizing bleed resistor R, with one pole, biasing pole BP connected to the charge collector/coupling capacitor, and the other pole, the sensing capacitor pole CP connected to the sensing capacitor. To further reduce noise, the sensing capacitor is connected to ground. The electrometer can then measure the voltage change on the sensing capacitor with respect to ground, as shown. These two grounding points can be combined to reduce electromagnetic noise further. The transformer T can be a step-up transformer as discussed above so that complex AC bias waveforms supplied here and to the bead electrode 9 can be generated inexpensively. For example, the step-up ratio can be 50. This arrangement greatly reduces drift and make accumulated charge sensing more accurate, where previously the coupling current of 100 pico-Amperes or less made drift and noise a real problem.

If desired, transformer T can be an isolation transformer, where the primary and secondary windings are separated by a Faraday cage. This can prevent coupling between the primary and secondary windings, where the primary winding acts as one capacitor plate, and the secondary as the other capacitor plate.

With this improved signal to drift ratio, the amount of charge sensed can decrease substantially. Measurements can now be made using a 1000 picoF capacitor as the sensing capacitor instead of the 0.1 µF value used previously. Also, the AC bias source as shown in FIGS. 10 and 11 can be separate from the AC waveform bias $V_9$ on the chuck, by delivering a separate AC bias to the charge collector/coupling capacitor directly, via a dedicated wire, electrode, bus, etc. This separate AC bias can be frequency matched or detuned with respect to $V_9$ to insure consistent correlation of the behavior of the charge collector/coupling capacitor to actual depositions.

Overall, too, these techniques allow $V_9$ biasing with voltage peaks much higher than previously possible. Using 8000 molecular weight polyethylene glycol as a substrate, bias peaks of 2 kV have been used. It is important also to keep in mind that any kind of bead transporter chuck can be used, including those that operate with bias electrodes directly exposed to the bead contact surface (such as illustrated in FIG. 12).

In practice, one introduces charged grains into the grain dispenser or container (not shown). For attracting and retaining negatively charged grains, for example, one can apply a negative bias to a conductive surface in the grain container and/or a tribo-charging mesh, and a positive bias to the bead electrode 9, while a grounded shield electrode 10 or a negatively biased shield electrode 10 helps guide grains to their intended destinations at the bead collection zones BCZ. This will function in sorting out grains according to polarity and charge/mass ratio, with grains of a certain charge/mass ratio and correct polarity being encouraged to seat themselves at the bead collection zones.

Available grain compositions are well known in the art, and are typically polymer-based, such as divinylbenzene copolymer; polystyrene; polyethylene glycol; or polyethylene glycol graft polystyrene, such as supplied under the trade name PEG-PS by PerSeptive Biosystems of Framingham, MA; or cross-linked polyethylene glycol resin, as supplied by Rapp Polymer GmbH of Germany. Grains can be dry, or may have absorbed or adsorbed an aqueous solution, or a fine powder, such as a micronized powder. Grains can also be, for example, dry paint or phosphor particles, or any other powders that can be charged, such as triboelectrically or by induction charging. The invention is very suited to depositing pharmaceuticals in a controlled manner onto substrate that can be used to form drug delivery vehicles. Dry deposition techniques as outlined herein allow excipients to be minimized in such formulations, which can facilitate quality control and eliminate issues of materials interacting in a deleterious fashion.

Grains can be charged prior to their application to the bead transporter chuck, for example, using plasma charging, or by the use of tribocharging (rubbing or contact charging) as known in the art. Materials that can be used for tribocharging include polytetrafluoroethylene (TEFLON®), and polymers of chlorotrifluoroethylene, chlorinated propylene, vinyl chloride, chlorinated ether, 4-chlorostyrene, 4-chloro-4-methoxy-styrene, sulfone, epichlorhydrin, styrene, ethylene, carbonate, ethylene vinyl acetate, methyl methacrylate, vinyl acetate, vinyl butyral, 2-vinyl pyridine styrene, nylon and ethylene oxide. See, for example, "Triboelectrification of Polymers" in K. C. Frisch and A. Patsis, *Electrical Properties of Polymers* (Technomic Publications, Westport, Conn.), which is hereby incorporated by reference in its entirety. Also see *Handbook of Electrostatic Processes*, Jen-shih Chang, Arnold J. Kelly, and Joseph M. Crowley, eds., Marcel Dekker, Inc., New York, ©1995. For example, polytetrafluoroethylene and polyethylene and other materials that become negatively charged tend to create a positive charge on the grain or object. Nylon and other materials that become positively charged will tend to create a negative charge on the grain or object. When using mechanical shaking to tribocharge polymer beads, it is preferred that the ratio of the amount or mass of tribocharging material used to charge the beads to the amount or mass of beads is such that their respective total surface areas are about equal.

In the course of using the bead transporter chucks, a number of operating modes can be used. For grain pickup or retention, a bead electrode, either exposed or unexposed to the bead contact surface, is electrically biased to attract grains, while other conductive surfaces in the grain dispenser or container can be biased oppositely. Any number of bead electrodes 9 can be used, and they can be individually and separately connected by known means to facilitate individual and selective addressing in two dimensions.

Once attracted and retained, grains on the bead transporter chuck are optionally transported to a substrate, microtiter plate, or other destination by moving the entire bead transporter chuck, or alternatively, the target substrate or plate is brought to the chuck. Beads are then released or discharged in a controlled manner when any or all of the applied voltages are reversed or set to zero. For example, for grain release, only the bead electrode 9 can be shorted out or grounded (0 volts), or have an opposite voltage applied. Optionally, when shield electrode 10 is used, it can be biased to be repulsive to grains during grain discharge. Acoustic releasing mechanisms or processes can be used to aid in grain discharge and placement.

When using bead transporter chucks according to the present invention, the temperature is preferably between −50° C. and 200° C., and more preferably between about 22° C. and 60° C. Relative humidity can be 0–100 percent, so long as condensation does not occur; more preferably the relative humidity is about 30 percent.

Bead electrodes 9 can comprise any number of separately addressable pixels or elements in two directions x and y, each having separately controlled bead collection zones. Any number of well known means and structures can be used to facilitate addressing as is known in the electrical and electronic arts. In this way, combinational synthesis or analysis can be simplified as discussed above. In using the bead transporter chucks, one can expose the bead contact surface of such a chuck to grains; selectively apply AC waveform voltages, such as the voltages given above, for each x-y addressable well, pixel, or individual spatial element of the chuck, to attract and retain grains selectively at each bead collection zone; then release the grains onto a desired destination aligned with the bead transporter chuck by selectively reversing or reducing voltages associated with each bead collection zone as required.

It is also possible that grains attracted by the chuck, especially large diameter grains or objects of large overall size, say 3 mm in diameter, and having low resistivity, can become viable substrates, to be coated with a pharmaceutically active compound. Such grains could include oblong shapes, made of water soluble film, such as hydroxypropyl methyl cellulose resin. See U.S. patent application Ser. No. 08/471,889, "Methods and Apparatus for Electronically Depositing a Medicament Powder Upon Predefined Regions of a Substrate," filed Jun. 6, 1995, now U.S. Pat. No. 5,714,007, and continuation-in-part thereof filed Jun. 6, 1996, Ser. No. 08/659,501, which documents are incorporated herein by reference in their entirety.

In this way, electrostatic chucks using low resistivity substrates, e.g., low resistivity substrates, can be scaled up for large scale continuous manufacturing, such as using a sheet of an edible substrate for use with tablets, for example, or a sheet of an inhaler substrate. For example, hydroxypropyl methyl cellulose can be used, such as Edisol M Film M-900 or EM 1100 available from Polymer Films Inc. (Rockville Conn.). Generally, sizing of grain diameters can range from less than one micron to 1000 microns or larger.

Obviously, many modifications and variations of the present invention are possible in light of the above teaching. It is therefore to be understood, that within the scope of the appended claims, the invention can be practiced otherwise than as specifically described or suggested here.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. An electrostatic chuck for attracting charged grains to a bead collection zone on a bead contact surface comprising:
    a bead electrode for selectively establishing a grain attracting field to the bead collection zone, the bead electrode shaped and configured in such a manner so that when an AC waveform potential is applied thereto, the grains are influenced by it and guided to selective retention by the bead electrode to the bead collection zone; and
    an electronic driver programmed to deliver the AC waveform potential configured to provide a repeated effective grain attraction potential at the bead collection zone, wherein the AC waveform potential comprises a grain-attracting potential pulse followed by a recovery period adapted to allow, in the case where the bead collection zone is formed on a substrate with a resistivity below $10^{11}$ $\Omega$-cm, an effective grain attraction field at the bead collection zone on activation of a subsequent grain-attracting potential pulse, wherein the AC waveform potential has a frequency of 100 Hz or less.

2. The electrostatic chuck of claim 1, further comprising a shield electrode which is shaped and configured to allow an electric field from the bead electrode to emanate through the bead collection zone.

3. The electrostatic chuck of claim 1, further comprising a floating pad electrode capacitively coupled to the bead electrode, wherein charge redistributions in the floating pad electrode in response to a potential applied to the bead electrode establish the grain attracting field.

4. The electrostatic chuck of claim 3, further comprising a shield electrode positioned and configured as to surround, but remain electrically isolated from, the floating pad electrode.

5. The electrostatic chuck of claim 1, further comprising a charge collector electrode for monitoring accumulated charge on the bead collection zone of the bead contact surface.

6. The electrostatic chuck of claim 1, further comprising a coupling capacitor positioned between the bead electrode and the bead contact surface, the coupling capacitor capacitively coupled to the bead collection zone on the bead contact surface.

7. The electrostatic chuck of claim 1, wherein the electronic driver is programmed to deliver the AC waveform potential configured such that the grain attraction potential on the bead collection zone is greater, on average, than that obtained when applying a time-averaged DC potential corresponding to the AC waveform potential.

8. The electrostatic chuck of claim 7, where the electronic driver is programmed to provide the AC waveform potential to maximize a grain attraction potential at the bead collection zone of the bead contact surface.

9. The electrostatic chuck of claim 1, wherein the electronic driver is programmed to deliver the AC waveform potential configured to provide a repeated effective grain attraction potential at the bead collection zone when the bead collection zone is formed on a substrate with a resistivity below $10^{10}$ $\Omega$-cm.

10. An electrostatic chuck device with an accumulated charge sensing circuit having a charge sensing electrode for monitoring accumulated charge on the bead collection zone of the bead contact surface, comprising:
    an AC bias source;
    an electrostatic chuck comprising at least one a bead electrode for establishing a grain attracting field to attract charged grain s to a bead collection zone the electrostatic chuck further comprising a sensing capacitor electrically connected between a charge collector electrode and the AC bias source; and
    an electrometer electrically connected between the AC bias source and a coupling capacitor to measure the potential of the sensing capacitor.

11. An accumulated charge sensing circuit of claim 10, comprising
    a transformer having a primary winding and a secondary winding, wherein the primary and secondary windings each have first and second poles;
    the charge collector electrode electrically connected to the first pole of the secondary winding of the transformer;
    the sensing capacitor connected between a ground and the second pole of the secondary winding of the transformer;
    the electrometer electrically connected between the second pole of the secondary winding of the transformer and a ground; and
    the AC bias source connected across the first and second poles of the primary winding of the transformer.

12. A method for adhering charged trains to a bead collection zone on a bead contact surface comprising:
    (1) adhering a substrate with a resistivity below $10^{11}$ $\Omega$-cm to an electrostatic chuck, with the substrate arrayed over a grain-attracting electrode of the electrostatic chuck so that a surface of the substrate defines the bead contact surface;
    (2) applying an AC waveform potential to the grain-attracting electrode to create a grain attracting field, wherein the AC waveform potential comprises a grain-attracting potential pulse followed by a recovery period adapted to allow an effective grain attraction potential at the bead collection zone on activation of a subsequent grain-attracting potential pulse, wherein the AC waveform potential has a frequency of 100 Hz or less; and
    (3) attracting and retaining a grain to the bead collection zone.

13. The method of claim 12, additionally comprising:

(4) reducing a first potential applied to the bead electrode, thereby reducing the grain attracting field sufficiently to discharge a grain from the bead collection zone to a desired location.

14. The method cf claim 12, additionally comprising:

(5) providing an accumulated charge sensing circuit for the bead transporter chuck having a charge sensing electrode for monitoring accumulated charge on a bead collection zone of the bead contact surface, comprising
   (a) an AC bias source, (2) a sensing capacitor electrically connected between the charge collector electrode and the AC bias source, and
   (b) an electrometer electrically connected between the AC bias source and the coupling capacitor to measure the potential the sensing capacitor;

(6) terminating the application of the AC waveform potential when the charge sensing circuit indicates that sufficient grains have been accumulated at the bead collection zone, or, where there are multiple bead collection zones and two or more charge sensing circuits, adjusting AC waveform potentials so that grain accumulation at various bead collection zones is adjusted.

15. The method of claim 12, wherein the AC waveform potential is effective to apply at least 300 µg/4 mm of charged powder to a said bead collection zone.

16. The method of claim 12, wherein the AC waveform potential is configured to provide a repeated effective grain attraction potential at the bead collection zone, even where a substrate defining the bead contact surface has a resistivity below $10^{10}$ Ω-cm.

17. The method of claim 16, wherein the AC waveform potential is effective to apply at least 300 µg/4 mm of charged powder to a said bead collection zone.

18. The method of claim 12, wherein the AC waveform potential is configured such that the grain attraction potential at the bead collection zone is greater, on average, than that obtained with a time-averaged DC potential corresponding to the AC waveform potential.

19. The method of claim 12, wherein the AC waveform potential is chosen to maximize a grain attraction potential at the bead collection zone of the bead contact surface.

20. The method of claim 12, wherein the grains are a micronized powder.

21. The method of claim 12, comprising fabricating dosage forms by:

providing an edible substrate as the substrate; and operating the electrostatic chuck pursuant to steps (1) through (3) to deposit measured amounts of powder, comprising a pharmaceutically active substance, on spatially resolved regions of the edible substrate.

22. The method of claim 12, wherein the AC waveform potential has a frequency of 25 Hz or less.

* * * * *

UNITED STATES PATENT AND TRADEMARK OFFICE
CERTIFICATE OF CORRECTION

PATENT NO. : 6,149,774
DATED : November 20, 2000
INVENTOR(S) : Sun et al.

It is certified that error appears in the above-identified patent and that said Letters Patent is hereby corrected as shown below:

<u>Column 26,</u>
Line 50, delete "trains" and insert -- grains --.

Signed and Sealed this

Twenty-third Day of April, 2002

Attest:

Attesting Officer

JAMES E. ROGAN
Director of the United States Patent and Trademark Office